United States Patent
Hang et al.

(10) Patent No.: US 10,199,583 B1
(45) Date of Patent: Feb. 5, 2019

(54) BLUE LUMINESCENT MATERIAL OF PLATINUM COMPLEX AND ORGANIC LIGHT-EMITTING DEVICE

(71) Applicants: Nanjing Tech University, Nanjing (CN); AAC Microtech (Changzhou) Co., Ltd., Changzhou (CN)

(72) Inventors: Xiaochun Hang, Shenzhen (CN); Junli Yin, Shenzhen (CN); Kang Shen, Shenzhen (CN); Yipei Wu, Shenzhen (CN); Tianshi Qin, Shenzhen (CN); Shaohai Chen, Saratoga, CA (US)

(73) Assignee: NANJING TECH UNIVERSITY, Changzhou, Jiangsu Province (CN)

( * ) Notice: Subject to any disclaimer, the term of this patent is extended or adjusted under 35 U.S.C. 154(b) by 0 days.

(21) Appl. No.: 16/133,990

(22) Filed: Sep. 18, 2018

(30) Foreign Application Priority Data

Jun. 22, 2018 (CN) .......................... 2018 1 0654510

(51) Int. Cl.
*C07F 15/00* (2006.01)
*H01L 51/50* (2006.01)
*H01L 51/00* (2006.01)
*C09K 11/06* (2006.01)

(52) U.S. Cl.
CPC ...... *H01L 51/0087* (2013.01); *C07F 15/0086* (2013.01); *C09K 11/06* (2013.01); *C09K 2211/1059* (2013.01); *C09K 2211/185* (2013.01); *H01L 51/5016* (2013.01)

(58) Field of Classification Search
CPC .......................... C07F 15/0086; H01L 51/5012
USPC ............................................. 546/10; 313/504
See application file for complete search history.

(56) References Cited

U.S. PATENT DOCUMENTS 9,450,195 B2 * 9/2016 Tsai ........................ C07F 17/02

* cited by examiner

*Primary Examiner* — Charanjit Aulakh
(74) *Attorney, Agent, or Firm* — Na Xu; IPro, PLLC

(57) ABSTRACT

The present disclosure provides a blue luminescent material, and the blue luminescent material is a tertradentate platinum complex having a chemical structure of Formula I comprising a pyridoimidazole carbene platinum structure. The blue luminescent material of the present disclosure may be used in OLED devices and apparatus as a dopant material and emits blue light having a wavelength of 450-490 nm. The present disclosure provides a design route for a material by introducing a pyridoimidazole-type carbene into the ligand of a platinum complex. Since the carbene structure has suitable triplet energy and its carbon-platinum bond is more stable than the nitrogen-platinum bond, the entire spectrum can become narrower, which will promote development of blue luminescent material and improve performances of the devices.

15 Claims, 9 Drawing Sheets

BLUE LUMINESCENT MATERIAL OF PLATINUM COMPLEX AND ORGANIC LIGHT-EMITTING DEVICE

CROSS-REFERENCE TO RELATED APPLICATIONS

The present application claims priority to Chinese Patent Application No. 201810654510.9, filed on Jun. 22, 2018, the content of which is incorporated herein by reference in its entirety.

TECHNICAL FIELD

The present disclosure relates to the technical field of electronic display and illumination technology, and specifically, to a multidentate platinum complex used as a blue luminescent material and an auxiliary luminescent material and to an organic light-emitting device including the platinum complex.

BACKGROUND

Compounds capable of absorbing and/or emitting light are applicable in a variety of optical and photoelectric devices, including but not limited to photo-absorbing devices such as solar- and light-sensitive devices, organic light-emitting diodes (OLEDs), light-emitting devices, devices capable of absorbing and emitting light and biological markers. In order to find organic and organometallic materials used in optical and photoelectric devices, many researchers have done associated studies. Generally, research in this area aims to find an applicable organic phosphorescent material. The primary goal in the fields of display and illumination fields is to improve stability of the materials and the devices, spectral characteristics and luminescent efficiency.

Despite significant advances in research devoted to photoelectric materials (e.g., red and green phosphorescent organometallic materials used as phosphors, and blue organometallic material used as fluorescent material), and success have been made in applications such as organic light emitting diode (OLED) illumination and advanced displays, there are still disadvantages in large-size display device applications, such as short luminescence lifetime, high heat release and low efficiency in actual applications. And these disadvantages can be proved by the marketed LG OLED television. Particularly, there is no effective way to solve the problem of the burn-in of TV channel logo after long-term fixed broadcast. From the prospective of application, in order to solve these problems, it is necessary to greatly improve the stability of materials and devices, and to set higher requirements on material design.

For the application of a small-sized OLED display (mainly used for mobile phone display) in which good effects are obtained, a blue fluorescent material is currently used, which has a low theoretical efficiency and does not belongs to a same system with other materials, thereby increasing the processing difficulty and cost. Therefore, improving the overall performance is the most important to solve the problem of blue phosphorescent materials and achieve stable light-emitting devices. Literature: Sinheui Kim, Hye Jin Bae, Sangho Park, Wook Kim, Joonghyuk Kim, Jong Soo Kim, Yongsik Jung, Soohwan Sul, Soo-Ghang Ihn, Changho Noh, Sunghan Kim and Youngmin You "Degradation of blue-phosphorescent organic light-emitting devices involves exciton-induced generation of polaron pair within emitting layers", Nat. Commun. 2018 vol. 9, no. 1, p. 1211.

Excellent blue luminescent materials, in particular high efficient blue phosphorescent material molecules having both a stable structure and a suitable luminescence spectrum, are particularly scarce. The lowest triplet excited state energy of the blue phosphors is much higher than that of the red and green phosphors, which means that the lowest triplet excited state energy of a host material of the blue devices should be even higher. Therefore, the organic structural units that can achieve the design of the blue luminescent range are limited, and thus it is more difficult to adjust the appropriate blue light spectrum. In addition, it needs to be able to exhibit excellent performance in the light-emitting process of the device. These require some specific and fundamental designs of structure.

Blue light is in a range of 400-500 nm (i.e. in a range of 400-495 nm or 400-490 nm). However, it is generally believed that blue light having short wavelength in a range of 400-450 nm (high energy blue light) is most harmful to eyes, can cause digital visual fatigue and affect sleep, and eventually cause eye pathological damages, such as myopia, cataracts, and macular degeneration, and break human rhythm. By designing a blue light source in a range of 450-500 nm and applying it to related electronic products, the problem of damages caused by the high-energy blue light in the current electronic devices can be solved.

Blue luminescent materials are used in OLED devices and apparatus as a dopant material, and their molecules participate in luminescence by stimulated emission of radiation as zero-dimensional points, which is the most demanding material in all OLED device structures in terms of stability. The literature, Wook Song and Jun Yeob Lee "*Degradation Mechanism and Lifetime Improvement Strategy for Blue Phosphorescent Organic Light-Emitting Diodes*" *Adv. Optical Mater.* 2017, briefly reports that the current stable blue light iridium complexes material having desirable stability, but none of the luminescent materials succeeded in controlling the majority of photoluminescence spectrum within the range of 450-490 nm. There remains a problem that emission color purity does not meet the requirement or that a large part of the light goes beyond the range of 450-490 nm, which needs to be filtered off, causing complicated process and waste of energy.

In terms of emission color purity, the tetradentate ligand-coordinated platinum complexes have the advantage that the energy level of spectral electronic vibration can be regulated, thereby achieving the goal of narrowing the spectrum and improving the color purity. Specific theoretical explanations can be found in reference Cong You, Fang Xia, Yue Zhao, Yin Zhang, Yongjian Sheng, Yipei Wu, Xiao-Chun Hang*, Fei Chen, Huili Ma, Kang Shen, Zhengyi Sun, Takahiro Ueba, Satoshi Kera, Cong Zhang, Honghai Zhang, Zhi-Kuan Chen, Wei Huang *Probing Triplet Excited States and Managing Blue Light Emission of Neutral Tetradentate Platinum (II) Complexes* 2018 *Journal of Physical Chemistry Letter*. Specific examples of applications of theory can be found in the patent application No. CN201810115217.5 (2018), titled Aryl-Substituted Tetradentate Ligand Coordinated Platinum Complexes, Synthesis Method And Use thereof, by Hang Xiaochun, Xia Fang, Sheng Yongjian, Qin Tianshi, Huang Wei.

In term of stability of metal complexes, the tetradentate ligand coordinated platinum compounds that have a given structure and contains a similar functional group are more stable than bidentate ligand coordinated iridium complexes, which is consistent with the conventional mechanism that higher chelating degree results in higher stability. An specific explanation may be that the iridium complex Ir(pmi)$_3$ containing phenylimidazole ligand is not stable and will gradually decomposes when placed in the air at room temperature. The literature Tissa Sajoto, Peter I. Djurovich, Arnold Tamayo, Muhammed Yousufuddin, Robert Bau and Mark E. Thompson *Ir(pmi)$_3$ Blue and Near-UV Phosphorescence from Iridium Complexes with Cyclometalated Pyrazolyl or N-Heterocyclic Carbene Ligands Inorganic Chemistry* 2005, 44, 7992-8003 describes a tetradentate ligand coordinated platinum complex PtON7, which also contains a phenylimidazole structure (pmi)NHC coordination, can exist stably. Moreover, high purity compounds can be prepared through purification by high temperature sublimation. Furthermore, associated devices have very high external quantum efficiency (EQE) and blue light luminescence spectra. The literature Xiao-Chun Hang, Tyler Fleetham, Eric Turner, Jason Brooks and Jian Li *Highly Efficient Blue-Emitting Cyclometalated Platinum(II) Complexes by Judicious Molecular Design Angew. Chem. Int. Ed.* 2013, 52, 6753-6756 demonstrates that the tetradentate ligand platinum complexes, whose structures are specially designed, are more stable than the iridium complexes and are more suitable to be used as a blue light dopant material in photoelectric devices.

In the NHC-coordinated blue light material, Ir(pmi)$_3$ is unstable. Enlarging the aromatic system of the NHC ring can improve the stability. For example, the iridium complex Ir(pmb)$_3$ with 2-phenylbenzoimidazole (pmb) used as its ligand has desirable stability, and the molecule itself is somewhat stable and will not decompose and change in a short time. Tissa Sajoto, Peter I. Djurovich, Arnold B. Tamayo, Jonas Oxgaard, William A. Goddard and Mark E. Thompson *Temperature Dependence of Blue Phosphorescent Cyclometalated Ir(III) Complexes J. Am. Chem. Soc.* 2009, 131, 9813-9822. The stability of the structure design is further improved, the 2-phenylpyridinoimidazole (pmp) coordinated iridium complexes Ir(pmp)$_3$ can exist stably, and the OLED blue light devices produced by using it provide a brightness greater than 22000 cd/m$^2$, literature: Jaesang Leel, Hsiao-Fan Chen, Thilini Batagoda, Caleb Coburn, Peter I. Djurovich, Mark E. Thompson and Stephen R. Forrest *Deep blue phosphorescent organic light-emitting diodes with very high brightness and efficiency* 2015 *Nature Materials*. This demonstrates that application of the structure unit pmp in dopant material and blue light dopant material provides improved device efficiency and stability.

Photoelectric devices using organic materials are becoming more and more popular, and there are many reasons for their popularity. Many of the materials used to make such devices are relatively inexpensive, and thus organic optoelectronic devices have potential cost advantages over inorganic devices. In addition, the inherent properties of organic materials, such as their flexibility, may make them well suited for special applications, such as processing on flexible substrates. Examples of organic photoelectric devices include organic light emitting devices (OLEDs), organic transistors, organic solar cells, and organic photoelectric detectors. For OLEDs, organic materials may have performance advantages over traditional materials. For example, the emission wavelength emitted by the organic light-emitting layer can usually be easily adjusted with a suitable dopant.

Light, i.e., fluorescence, is produced when the exciton experiences decay from the singlet excited state to the ground state. Cold light, i.e., phosphorescence, is produced when the exciton experiences decay from the triplet excited state to the ground state. Because the strong spin-orbit coupling of heavy metal atoms can very effectively enhance the intersystem crossing (ISC) between the singlet excited state and the triplet excited state, phosphorescent metal complexes, such as platinum complexes, have showed the potential to harvest both the singlet and the triplet excited states and to reach 100% internal quantum efficiency. Therefore, the phosphorescent metal complex is a good candidate for the dopant of the light-emitting layer in an organic light-emitting device (OLED) and has attracted much attention from both academic and industrial fields. Moreover, in the past decade, certain achievements have been made on the road to high-margin commercialization of this technology. For example, OLEDs have been applied in advanced displays for smartphones, televisions and digital cameras.

However, blue electroluminescent devices remains so far the most challenging area of the technology, at least in part due to the instability of blue devices. It is generally recognized that the choice of matrix material is a factor affecting the stability of the blue devices. However, the blue phosphorescent material has very high the lowest triplet excited state ($T_1$) energy, this generally means that the lowest triplet excited state ($T_1$) energy of the matrix material of the blue devices should be higher, bringing difficulties to the development of the matrix materials for the blue devices. Therefore, it is necessary to develop a blue luminescent material with superior performance.

SUMMARY

The present disclosure relates to a series of platinum complexes applicable in organic light emitting diodes (OLEDs) and technologies of display and illumination as emitters. The platinum complex according to the present disclosure has a structure of Formula I:

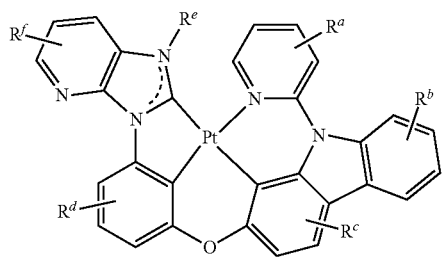

Formula I in which each of $R^a$, $R^b$, $R^c$, $R^d$ and $R^f$ is independently selected from: (1) hydrogen $^1$H and isotope thereof, and any other monoatomic substituents (such as fluorine, chlorine or the like); or (2) alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, polymeric groups; or substituents containing isotopes;

each of $R^a$, $R^b$, $R^c$, $R^d$ and $R^f$ is a mono-, di-, tri- or tetra-substitutions, which means that the aryl ring to which $R^a$, $R^b$, $R^c$, $R^d$ or $R^f$ is bonded has one, two, three, or four substituents of $R^a$, $R^b$, $R^c$, $R^d$ or $R^f$. The position of substitution and the maximum of substituents depend on the substitution status of the aryl ring to which $R^a$, $R^b$, $R^c$, $R^d$ or $R^f$ is bonded.

$R^e$ is any one selected from alkyl, aryl-substituted alkyl, fluorine-substituted alkyl, aryl, alkyl-substituted aryl, aryl-substituted aryl, cycloalkyl, alkyl; alkyl or aryl substituted by other groups.

In an embodiment of the platinum complex according to the present disclosure, each of $R^a$, $R^b$, $R^c$, $R^d$ and $R^f$ is independently selected from monoatomic substituents of ruthenium (D), ruthenium (T), fluorine (F), chlorine (Cl) bromine (Br) or iodine (I).

In some embodiments of the platinum complexes according to the present disclosure, each of $R^a$, $R^b$, $R^c$, $R^d$, $R^e$ and $R^f$ is independently selected from alkyl- or aryl-substituted alkyl. In this case, each of $R^a$, $R^b$, $R^c$, $R^d$, $R^e$ and $R^f$ can be, but not limited to, an alkyl group, such as methyl, benzyl (phenylmethyl), diphenylmethyl, triphenylmethyl; ethyl, 2-phenylethyl, 2,2-diphenylethyl, 2,2,2-trifluoroethyl; propyl, isopropyl, 3,3,3-trifluoropropyl, 1,1,1,3,3,3-hexafluoro-2-propyl; butyl, isobutyl, hexafluoroisobutyl, tert-butyl; cyclopropyl, cyclobutyl, cyclopentyl, cyclohexyl, cycloheptyl or the like.

In some embodiments of the platinum complex of the present disclosure, each of $R^a$, $R^b$, $R^c$, $R^d$, $R^e$ and $R^f$ is independently aryl or alkyl-substituted aryl. In this case, each of $R^a$, $R^b$, $R^c$, $R^d$, $R^e$ and $R^f$ can be, but not limited to, an aryl group, such as phenyl, 2-methylphenyl, 2-isopropylphenyl, 2-ethylphenyl, 4-methylphenyl, 4-isopropylphenyl, 4-ethylphenyl, 4-tert-butylphenyl, 2,4-dimethylphenyl, 2,4-diethylphenyl, 2,4-diisopropylphenyl, 2,6-dimethylphenyl, 3,5-dimethylphenyl, 2,3,5,6-tetramethylphenyl, 2,4,6-trimethylphenyl, or the like.

In some more specific embodiments of the platinum complex according to the present disclosure, $R^e$ is an alkyl substituent, and each of $R^a$, $R^b$, $R^c$, $R^d$ and $R^f$ is independently selected from an alkyl substituent or a monoatom. Examples are as follows:

In the platinum complex as shown in Example Complex 1, W is methyl, and each of $R^a$, $R^b$, $R^c$, $R^d$ and $R^f$ is hydrogen;

In the platinum complex as shown in Example Complex 2, W is methyl, $R^f$ is methyl, and each of $R^a$, $R^b$, $R^c$ and $R^d$ is hydrogen;

In the platinum complex as shown in Example Complex 3, W is methyl, $R^f$ is methyl, $R^a$ is fluorine, and each of $R^b$, $R^c$ and $R^d$ is hydrogen;

In the platinum complex as shown in Example Complex 4, W is methyl, $R^f$ is methyl, $R^a$ is deuterium, and each of $R^b$, $R^c$ and $R^d$ is hydrogen;

In the platinum complex as shown in Example Complex 5, W is methyl, $R^f$ is methyl, $R^a$ is methyl ($CD_3$) where hydrogen ($^1H$) is substituted by an isotope ($^2H$, i.e. D), and each of $R^b$, $R^c$ and $R^d$ is hydrogen;

In the platinum complex as shown in Example Complex 6, $R^e$ is methyl, and each of $R^a$, $R^b$, $R^c$, $R^d$ and $R^f$ is methyl.

Example Complex 1

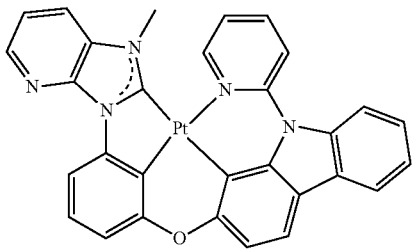

Example Complex 2

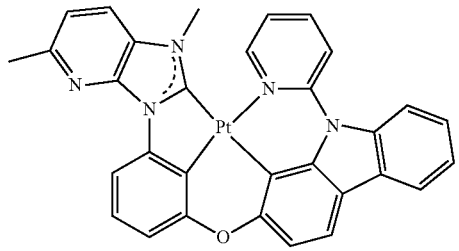

Example Complex 3

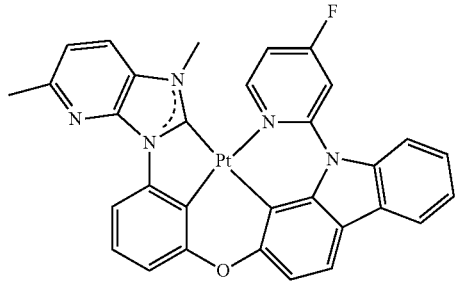

Example Complex 4

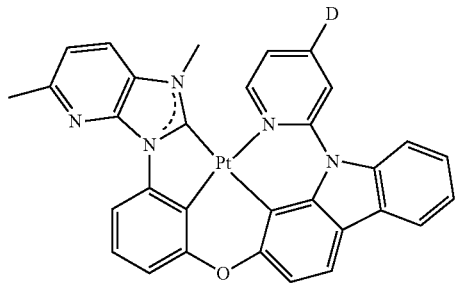

Example Complex 5

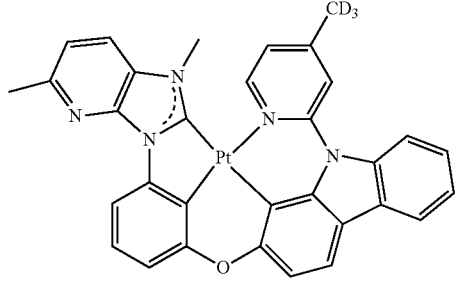

Example Complex 6

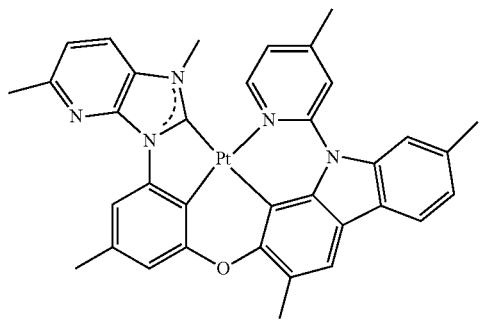

It has been found in the tests that the platinum complexes containing D (deuterium) or deuterated group —CD$_3$ have a narrower luminescence spectrum, and a full width at half maximum can be smaller than 25 nm.

Optionally, R$^a$ can be fused with adjacent carbazole to form a ring, that is, a bridging structure, such as —C(R$^h$)$_2$—, —Si(R$^h$)$_2$—, —O— or —NR$^h$—, can be formed between the aromatic ring to which R$^a$ is bonded and the aromatic ring to which R$^b$ is bonded. In this case, the platinum complex has a structure as shown in formula II to formula V.

Formula II

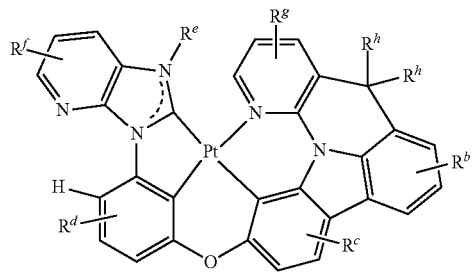

Formula III

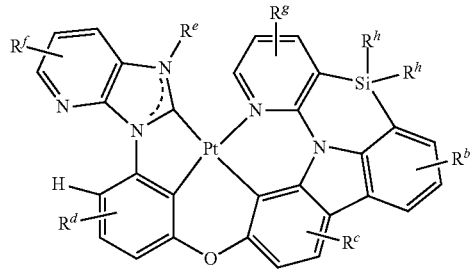

Formula IV

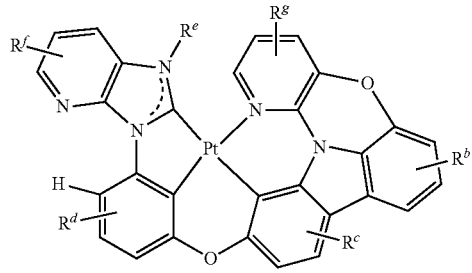

Formula V

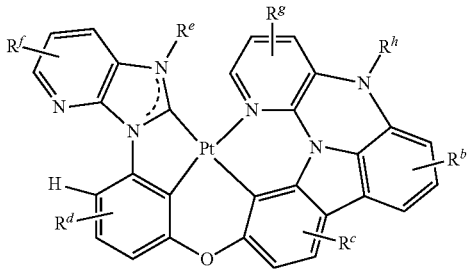

R$^g$ is selected from: (1) hydrogen atom, its isotopes, and any other monoatomic substituents; or (2) alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, polymeric groups, or substituents containing isotopes (for example, deuterated methyl);

R$^h$ is selected from alkyl, aryl-substituted alkyl, fluorine-substituted alkyl, aryl, alkyl-substituted aryl, aryl-substituted aryl; cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, polymeric groups, or substituents containing isotopes.

The present disclosure provides the structures of a plurality of platinum complexes according to the present application.

The present disclosure further provides a method for synthesizing the platinum complexes according to the present application.

The present disclosure further discloses simulated and calculated properties of the platinum complexes according to the present application.

The present disclosure further discloses structural characterization data of the platinum complexes according to the present application.

The platinum complex according to the present application can also be used as a photoelectric material, a photoluminescent material, a blue luminescent material, or a phosphorescent material.

The present disclosure also discloses a spectrum and characterization data for the related luminescent properties of the platinum complex used as a phosphorescent material.

The platinum complex described in the present disclosure can be used as a luminescent material of a light-emitting layer, as a host material of a light-emitting layer, or as a guest material of a light-emitting layer in an organic photoelectric device.

The present disclosure also discloses an organic light-emitting diode (OLED) device emitting blue light and comprising the platinum complex according to the present disclosure, a methods for manufacturing the device, and electroluminescence data.

The present disclosure provides a design route of a material by introducing a pyridoimidazole-type carbene into a ligand of platinum complex. Since the carbene structure has suitable triplet energy and has a carbon-platinum bond that is more stable than the nitrogen-platinum bond, the entire spectrum can become narrower, which will promote emission of light color and improve performances of the device. The present disclosure provides a divalent platinum complex of a neutral tetradentate ligand having a pyridoimidazole carbene platinum structure. The complex, as a phosphorescent material, is capable of emitting blue light, stable, efficient, and has a narrow wavelength range which falls within a range of long-wavelength blue light. Therefore, the complex is completely suitable to be used as an organic blue light emitters in OLED-related products. In addition, it is easy to prepare this complex and purify it by sublimation, the complex is soluble in common organic solvents, and adapts to both evaporation process and the solution process. Such material has characters of low energy and high color purity, which comprehensively surpass the current fluorescent materials, and will change the situation of a lack of stable and high-efficiency blue-light dopant for current flat panel display, and improve light emission and device performance. More specifically, CIE coordinates and luminous efficiency of this stable complex will be adjust to match the needs of flat panel display.

BRIEF DESCRIPTION OF DRAWINGS

FIG. 2 illustrates a distribution of highest occupied molecular orbital (HOMO) and lowest unoccupied molecular orbital (LUMO) of complex 103. HOMO and LUMO is in an up-down separation mode. HOMO is similar to the HOMO of the PtON series platinum complexes, such as PtON1 and PtON7, and LUMO is more evenly distributed in the pyridine and pyridoimidazole moieties and exhibits a spatial delocalization pattern.

energy efficiency, and (c) external quantum efficiency. FIG. 11 illustrates that efficiency in the photoelectric conversion of an OLED having a structure of ITO/PEDOT:PSS (70 nm)/MCP:complex 101 (95:5, 40 nm)/DPEPO (10 nm)/TmPyPB (50 nm)/Liq (1 nm)/Al (100 nm) can be characterized and described by (a) current efficiency, (b) energy efficiency, and (c) external quantum efficiency. The highest current efficiency, the highest energy efficiency and the highest external quantum efficiency of the photoelectric conversion of the device containing complex 101 are 12 cd/A, 19 lm/W and 11%, respectively, indicating that the complex 101 as a blue luminescent dopant has efficient photoelectric conversion performance.

DESCRIPTION OF EMBODIMENTS

Figure 1:
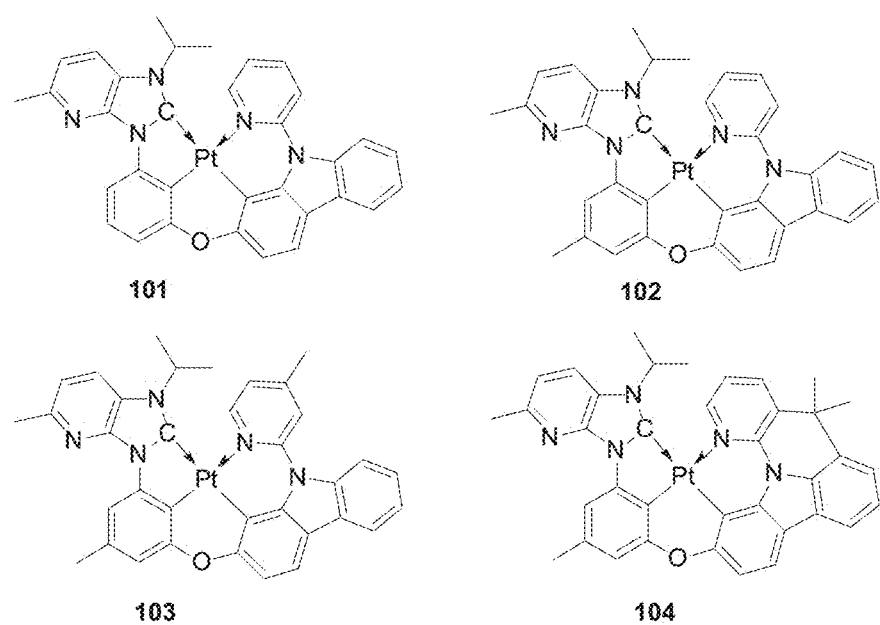
FIG. 1 illustrates structures of four representative platinum complexes (complexes 101-104) according to the present application, where complex 104 represents structure II in which substituent $R^a$ is bonded to an adjacent carbazole to form a fused ring, indicating that formula II-IV also possess material properties of formula I. Complex 104 is a special case of the complex as shown in formula I.
Figure 2:
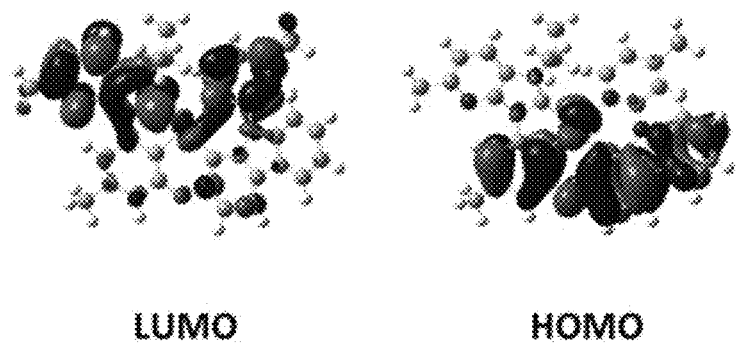
FIG. 2 shows a frontier orbital distribution of complex 103.
Figure 3:
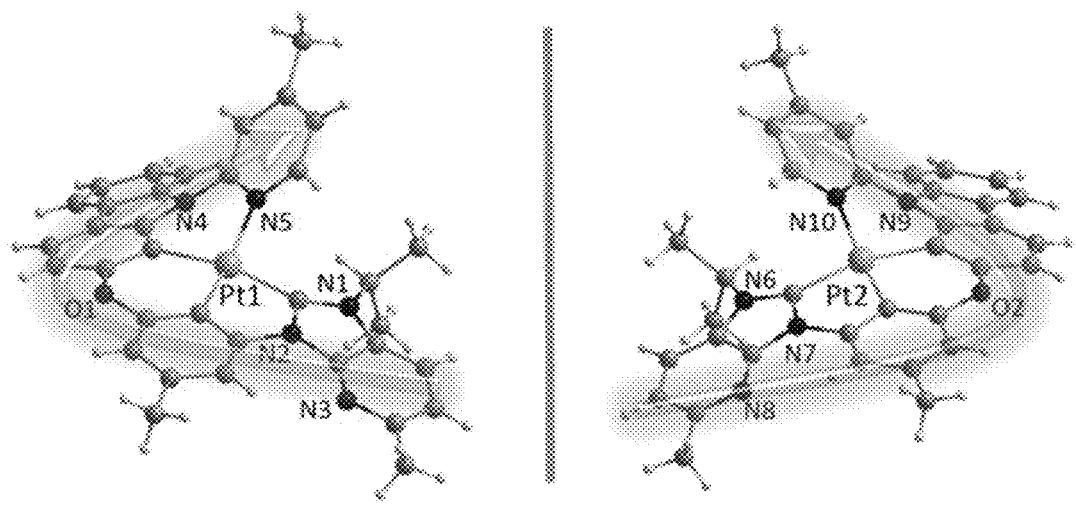
FIG. 3 is a molecular structure diagram of a single-molecule and stacked molecules of complex 103, using single-crystal diffraction. The molecular structure diagram shows two enantiomers, indicating that this platinum complex can be chirally differentiated and separated, and a single isomer has circular dichroism and circularly polarized luminescence effects. Reference: *Circularly Polarized Luminescence Spectroscopy* JAMES P. RIEHL *Chemical Reviews* 1986 01-16. The molecular structure diagram indicates a weak hydrogen bond in molecules and a six-membered inner ring structure formed with the adjacent structure, which is favorable to the stability of the molecular structure.
Figure 4:
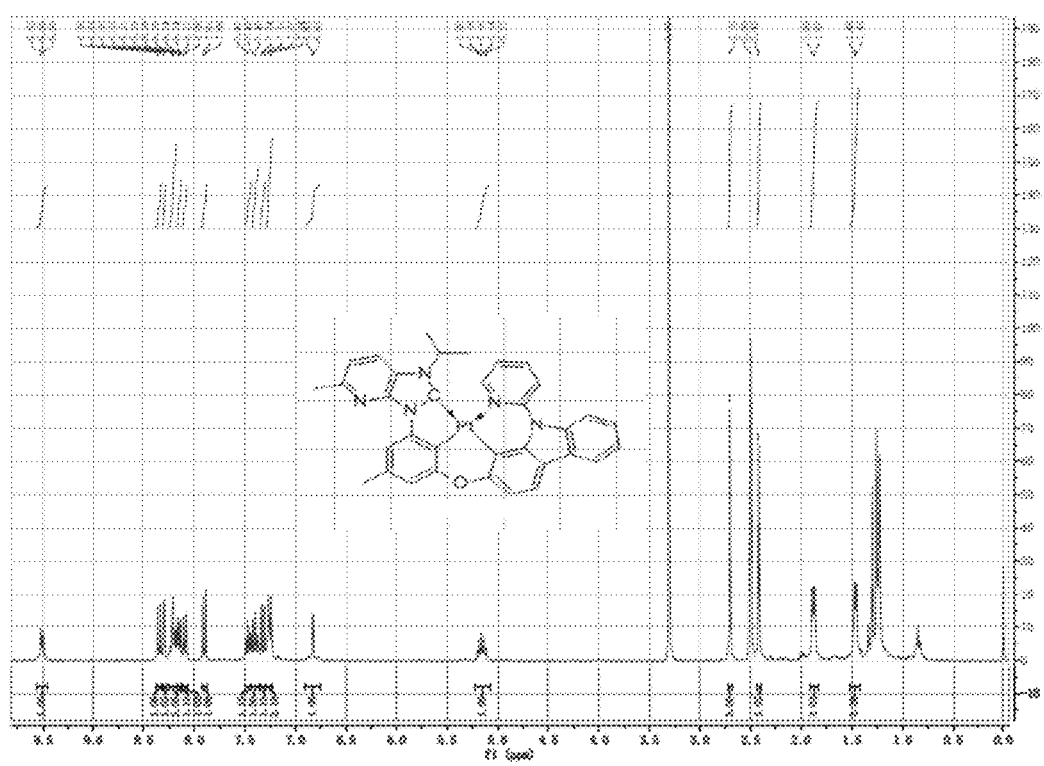
FIG. 4 is a $^1$H-NMR spectrum of a single molecule of complex 102. The spectrum indicates that this complex may exist separately and stably, and can be purified and characterized. In the NMR spectrum, in addition to the stable structural of the platinum complex, the platinum complex does not show a signal in an aggregated form, indicating that this platinum complex molecule is separated from one another in a solution.
Figure 5:
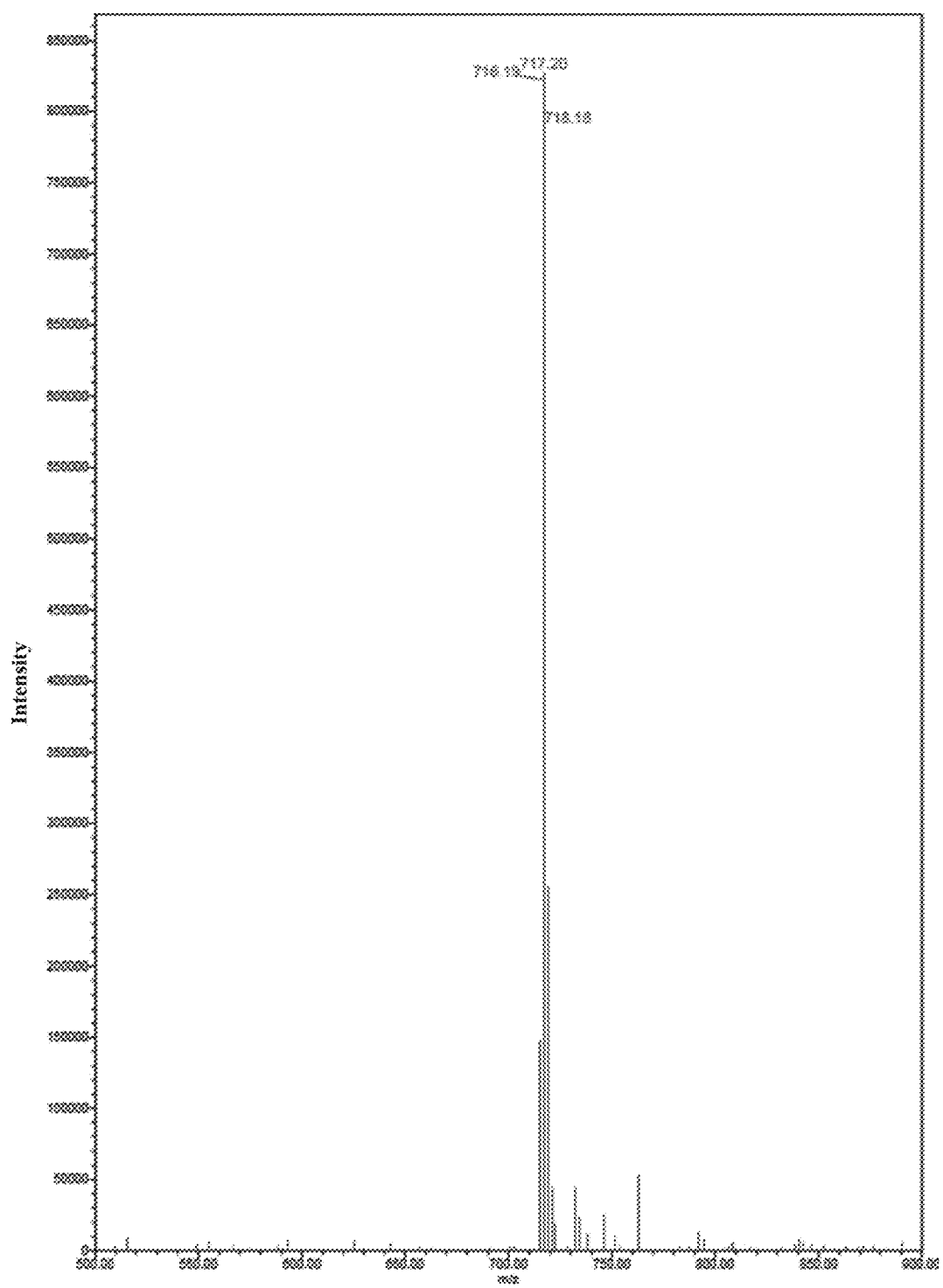
FIG. 5 shows a mass spectrum of complex 102.
Figure 6:
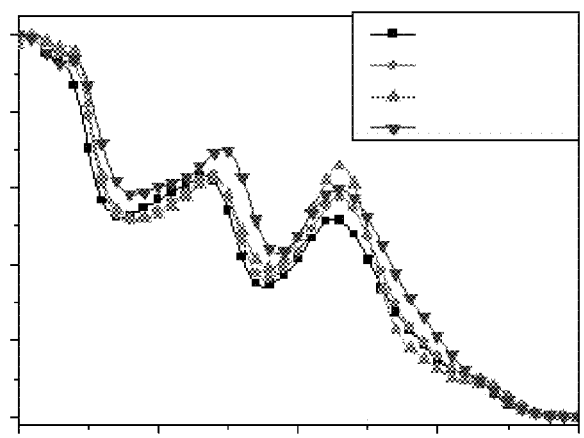
FIG. 6 shows a UV-Vis absorption spectrum of complexes 101-104 at room temperature. The absorption spectrum exhibits a very strong absorption at a long-wavelength range of 280-420 nm, which is different from that of the ligand precursor. In a range of 280-330 nm, a π-π* transition occurs in the carbazole-center of the complex, which is similar to PtON7. The absorption peak behind 330 nm can be designated as a valence transfer transition (MLCT) between a central metal ion of the complex and a ligand. In the platinum complex, this transition occurs strongly, a kurtosis thereof can reach a half of an absorption kurtosis of the ligand, and a extinction coefficient can reach $2.5 \times 10^{-4}$· $M^{-1} \cdot cm^{-1}$. This indicates that this molecule has a high energy absorbing efficiency and can be used as a preferred molecular structure of a dopant molecule.
Figure 7:
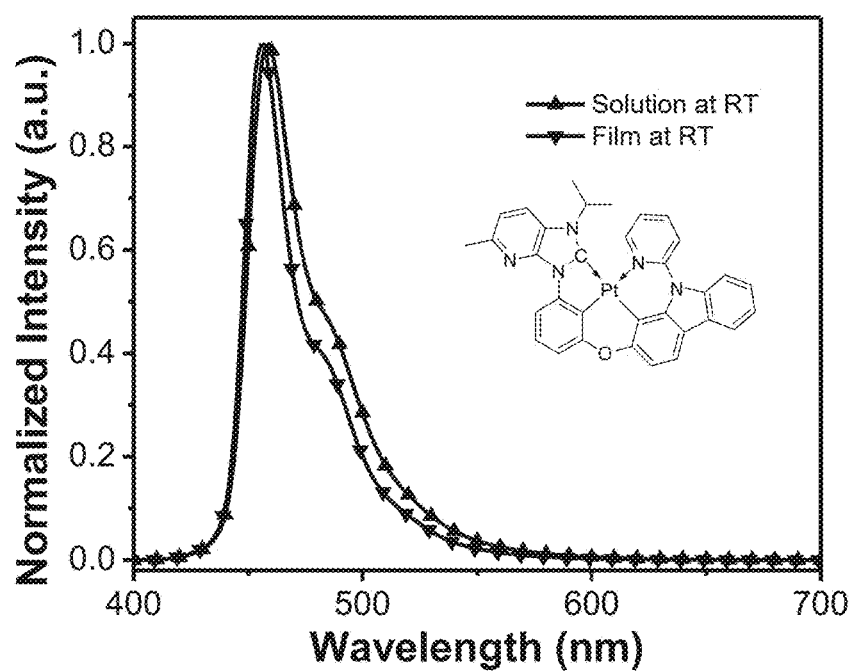
FIG. 7 shows a phosphorescence emission spectrum of complex 101 in $CH_2Cl_2$ and in PMMA (polymethyl methacrylate) at room temperature. The emission spectrum indicates that the luminescence spectrum of the complex 101 falls into the blue light range, and has a narrow full width at half maximum. The emission peak value in the PMMA film is at 456 nm, and the full width at half maximum is 24 nm, in which a number of photons in the effective blue light range exceeds 75%.

The present disclosure will be further described with examples and comparative examples, these examples are merely used to explain the present disclosure, and the present disclosure is not limited to the following examples. Modifications or equivalent substitutions of technical solutions in the present disclosure, without departing from the spirit and scope, shall fall within the scope of the present disclosure. The present disclosure can be understood more readily by reference to the following detailed description and the Examples included therein.

It is to be understood that, the present platinum complexes, devices, and/or methods disclosed and described herein are not limited to a specific synthetic method or to particular reagents, unless otherwise specified. It is also to be understood that the terms used herein are merely for the purpose of describing particular aspects, but not intended to limit them. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, "a component" also includes a mixture of two or more components.

As used herein, the expressions "optional" or "optionally" means that the subsequently described issue or circumstance may or may not occur, and that the description includes instances where the said issue or circumstance occurs and instances where it does not.

As referred to herein, a linking atom or group can connect two atoms such as, for example, a N atom and a C atom. A linking atom or group is disclosed as X, Y, $Y^1$, $Y^2$, and/or Z herein. The linking atom can optionally, if valency is present, have other chemical moieties. For example, on one hand, oxygen would not have any other chemical groups attached as the valency is satisfied once it is bonded to two groups (e.g., N and/or C groups), on the other hand, when carbon is the linking atom, two additional chemical moieties can be attached to the carbon. Suitable chemical moieties include amine, amide, thiol, aryl, heteroaryl, cycloalkyl, and heterocyclyl moieties.

As used herein, the expression "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and can be the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the expressions "substitution" or "substituted with" imply that such substitution is in accordance with permitted valence of the substituted atom and the substituent, and the substitution results in a stable compound, e.g., a compound that does not spontaneously undergo transformation such as rearrangement, cyclization, elimination, etc. It also can be interpreted that, in certain aspects, unless indicated otherwise, individual substituents can be further substituted (i.e., further substituted or unsubstituted).

As used herein, the term "substituent" refers to group for replacing hydrogen of an organic compound, including isotopes of hydrogen, such as deuterium (D) or tritium (T), except hydrogen itself.

The term "alkyl" as used herein is a branched or unbranched saturated hydrocarbon group consisting of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more substituents including, but not limited to, alkyl, cycloalkyl, alkoxy, amino, ether, halide, hydroxy, nitro, silyl, sulfo-oxo, or thiol, as described herein. A "small alkyl" group is an alkyl group containing 1 to 6 (e.g., from 1 to 4) carbon atoms.

Throughout the specification, "alkyl" is generally used to refer to both unsubstituted alkyl group and substituted alkyl group. However, the substituted alkyl group is a specific one by identifying the specific substituent(s) on the alkyl group. For example, the term "halogenated alkyl" or "haloalkyl" specifically refers to an alkyl group substituted with one or more halides, e.g., fluorine, chlorine, bromine, or iodine. The term "alkoxyalkyl" specifically refers to an alkyl group substituted with one or more alkoxy groups, as described below. The term "alkylamino" specifically refers to an alkyl group that is substituted with one or more amino groups, as described below. When "alkyl" is used in an embodiment and "alkylalcohol" is used in another embodiment, it is not meant to imply that the term "alkyl" also refers to specific terms such as "alkylalcohol" and the like.

The above also can be adapted to other groups described herein. That is, when a term such as "cycloalkyl" refers to unsubstituted and substituted cycloalkyl, the substituent may be specifically identified herein. For example, a specific substituted cycloalkyl can be referred to as "alkylcycloalkyl". Similarly, a substituted alkoxy can be specifically referred to as, e.g., a "halogenated alkoxy", a particular substituted alkenyl can be, e.g., an "alkenylalcohol" or the like. Again, using a general term such as "cycloalkyl" and a specific term such as "alkylcycloalkyl" is not intended to imply that the general term does not include the specific term.

The term "cycloalkyl" as used herein is a non-aromatic ring based on carbon and consisting of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a cycloalkyl group as defined above, and is included within the scope of "cycloalkyl". Under the definition, at least one carbon atom of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more substituents including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by a formula —$(CH_2)_a$—, where "a" is an integer from 2 to 500.

The terms "alkoxy" and "alkoxyl" as used herein to refer to an alkyl or cycloalkyl group bonded via an ether linkage. That is, an "alkoxy" group can be defined as —$OA^1$, where $A^1$ is alkyl or cycloalkyl as defined above. "Alkoxy" also includes polymers of alkoxy groups described above. That is, an alkoxy group can be a polyether such as —$OA^1$-$OA^2$ or —$OA^1$-$(OA^2)_a$-$OA^3$, where "a" is an integer from 1 to 200, and $A^1$, $A^2$ and $A^3$ are alkyl and/or cycloalkyl groups.

The term "alkenyl" as used herein is a hydrocarbon group consisting of 2 to 24 carbon atoms, and a structural formula thereof contains at least one carbon-carbon double bond. An asymmetric structure such as $(A^1A^2)C=C(A^3A^4)$ is intended to include both E and Z isomers. It can be concluded from the structural formula that an asymmetric alkene is present, which can be explicitly indicated by C=C. The alkenyl group can be substituted with one or more substituents including, but not limited to, alkyl, cycloalkyl, alkoxy, alkenyl, cycloalkenyl, alkynyl, cycloalkynyl, aryl, heteroaryl, aldehyde, amino, carboxylic acid, ester group, ether, halide, hydroxy, ketone, azide, nitro, silyl, sulfo-oxo, or thiol, as described herein.

The term "cycloalkenyl" as used herein is a non-aromatic carbon-based ring consisting of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the definition of "cycloalkenyl", where at least one of carbon atoms on the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more substituents including, but not limited to, alkyl, cycloalkyl, alkoxy, alkenyl, cycloalkenyl, alkynyl, cycloalkynyl, aryl, heteroaryl, aldehyde, amino, carboxylic acid, ester group, ether, halide, hydroxy, ketone, azide, nitro, silyl, sulfo-oxo, or thiol as described herein.

The term "alkynyl" as used herein is a hydrocarbon group consisting of 2 to 24 carbon atoms, and a structural formula thereof contains at least one carbon-carbon triple bond. The alkynyl group can be unsubstituted or substituted with one or more substituents including, but not limited to, alkyl, cycloalkyl, alkoxy, alkenyl, cycloalkenyl, alkynyl, cycloalkynyl, aryl, heteroaryl, aldehyde, amino, carboxylic acid, ester group, ether, halide, hydroxy, ketone, azide, nitro, silyl, sulfo-oxo, or thiol, as described herein.

The term "cycloalkynyl" as used herein is a non-aromatic carbon-based ring consisting of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl as defined above, and is included within the definition of "cycloalkynyl", where at least one carbon atom on the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more substituents including, but not limited to, alkyl, cycloalkyl, alkoxy, alkenyl, cycloalkenyl, alkynyl, cycloalkynyl, aryl, heteroaryl, aldehyde, amino, carboxylic acid, ester group, ether, halide, hydroxy, ketone, azide, nitro, silyl, sulfo-oxo, or thiol as described herein.

The term "aryl" as used herein is a group containing any carbon-based aromatic group including, but not limited to, benzene, naphthalene, phenyl, biphenyl, phenoxybenzene, and the like. The term "aryl" also includes "heteroaryl", which is defined as a group including an aromatic group with at least one heteroatom incorporated in the ring of the aromatic group. Examples of heteroatoms include, but are not limited to, nitrogen, oxygen, sulfur, and phosphorus. Likewise, the term "non-heteroaryl", which is also included in the term "aryl", defines a group that contains an aromatic group without heteroatom. The aryl group can be substituted or unsubstituted. The aryl group can be substituted with one or more substituents including, but not limited to, alkyl, cycloalkyl, alkoxy, alkenyl, cycloalkenyl, alkynyl, cycloalkynyl, aryl, heteroaryl, aldehyde, amino, carboxylic acid, ester group, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups bonded via a fused ring structure, such as naphthalene, or bonded via one or more carbon-carbon bonds, such as biphenyl.

The term "aldehyde" as used herein is represented by a formula —C(O)H. Throughout this specification "C(O)" is a notation of a carbonyl group, i.e., C=O.

The terms "amine" or "amino" as used herein are represented by a formula —$NA^1A^2$, where $A^1$ and $A^2$ can be, independently, hydrogen, alkyl, cycloalkyl, alkenyl, cycloalkenyl, alkynyl, cycloalkynyl, aryl, or heteroaryl group, as described herein.

The term "alkylamino" as used herein is represented by a formula —NH(-alkyl), where alkyl is described above. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by a formula —$N(-alkyl)_2$, where alkyl is described above. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by a formula —C(O)OH.

The term "ester group" as used herein is represented by a formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by a formula -$(A^1O(O)C-A^2-C(O)O)_a$— or -$(A^1O(O)C-A^2-OC(O))_a$—, where $A^1$ and $A^2$ can be, independently, alkyl, cycloalkyl, alkenyl, cycloalkenyl, alkynyl, cycloalkynyl, aryl, or heteroaryl group as described herein, and "a" is an integer from 1 to 500. "Polyester" is a term used to describe a group that is produced by a reaction between a compound having at least two carboxylic acid groups and a compound having at least two hydroxyl groups.

The term "ether" as used herein is represented by a formula $A^1OA^2$, where $A^1$ and $A^2$ can be, independently, alkyl, cycloalkyl, alkenyl, cycloalkenyl, alkynyl, cycloalkynyl, aryl, or heteroaryl group as described herein. The term "polyether" as used herein is represented by a formula $-(A^1O-A^2O)_a-$, where $A^1$ and $A^2$ can be, independently, alkyl, cycloalkyl, alkenyl, cycloalkenyl, alkynyl, cycloalkynyl, aryl, or heteroaryl group as described herein, and "a" is an integer from 1 to 500. Examples of polyether group include polyethylene oxide, polypropylene oxide, and polybutylene oxide.

The term "polymeric" includes polyalkylene, polyether, polyester, and other groups containing repeating units. The repeating unit can be, but not limited to $-(CH_2O)_n-CH_3$, $-(CH_2CH_2O)_n-CH_3$, $-[CH_2CH(CH_3)]_n-CH_3$, $-[CH_2CH(COOCH_3)]_n-CH_3$, $-[CH_2CH(COOCH_2CH_3)]_n-CH_3$, and $-[CH_2CH(COO^tBu)]_n-CH_3$, where n is an integer (e.g., n>1 or n>2).

The term "halide" as used herein refers to halogens, such as fluorine, chlorine, bromine, or iodine.

The term "heterocyclyl" as used herein refers to a single ring and multi-ring non-aromatic ring systems in which at least one ring is other than a carbon ring. This term includes azetidine, dioxane, furan, imidazole, isothiazole, isoxazole, morpholine, oxazole, oxazole such as 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine such as 1,2,4,5-tetrazine, tetrazole such as 1,2,3,4-tetrazole and 1,2,4,5-tetrazole, thiadiazole such as 1,2,3-thiadiazole, 1,2,5-thiadiazole and 1,3,4-thiadiazole, thiazole, thiophene, triazine such as 1,3,5-triazine and 1,2,4-triazine, triazole such as 1,2,3-triazole, 1,3,4-triazole, or the like.

The term "hydroxyl" as used herein is represented by a formula —OH.

The term "ketone" as used herein is represented by a formula $A^1C(O)A^2$, where $A^1$ and $A^2$ can be, independently, alkyl, cycloalkyl, alkenyl, cycloalkenyl, alkynyl, cycloalkynyl, aryl, or heteroaryl group as described herein.

The term "azide" as used herein is represented by a formula —$N_3$.

The term "nitro" as used herein is represented by a formula —$NO_2$.

The term "nitrile" as used herein is represented by a formula —CN.

The term "silyl" as used herein is represented by the formula —$SiA^1A^2A^3$, where $A^1$, $A^2$ and $A^3$ can be, independently, hydrogen, alkyl, cycloalkyl, alkoxy, alkenyl, cycloalkenyl, alkynyl, cycloalkynyl, aryl, or heteroaryl as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen, alkyl, cycloalkyl, alkenyl, cycloalkenyl, alkynyl, cycloalkynyl, aryl, or heteroaryl group as described herein. Throughout this specification, "S(O)" is a notation for S=O. The term "sulfonyl" is used herein to refer to the sulfo-oxo group represented by the formula —$S(O)_2A^1$, where $A^1$ can be hydrogen, alkyl, cycloalkyl, alkenyl, cycloalkenyl, alkynyl, cycloalkynyl, aryl, or heteroaryl group as described herein. The term "sulfone" as used herein is represented by a formula $A^1S(O)_2A^2$, where $A^1$ and $A^2$ can be, independently, alkyl, cycloalkyl, alkenyl, cycloalkenyl, alkynyl, cycloalkynyl, aryl, or heteroaryl group as described herein. The term "sulfoxide" as used herein is represented by a formula $A^1S(O)A^2$, where $A^1$ and $A^2$ can be, independently, alkyl, cycloalkyl, alkenyl, cycloalkenyl, alkynyl, cycloalkynyl, aryl, or heteroaryl as described herein.

The term "thiol" as used herein is represented by a formula —SH.

"$R^1$", "$R^2$", "$R^3$", "$R^n$", where n is an integer, can independently include one or more of the groups listed above. For example, if $R^1$ is a straight chain alkyl group, one hydrogen atom of the alkyl group can optionally be substituted with hydroxyl, alkoxy, alkyl, halide, or the like. Depending upon the selected groups, a first group can be incorporated in a second group, or the first group can be bonded (i.e., attached) to the second group. For example, with the phrase "an alkyl group comprising an amino group", the amino group can be included in the backbone of the alkyl group. Alternatively, the amino group can be attached to the backbone of the alkyl group. The property of the selected group will determine whether the first group is embedded in or attached to the second group.

Compounds described herein may contain "optionally substituted" moieties. In general, the term "substituted" means that one or more hydrogen atoms of the designated moiety are replaced with a suitable substituent, no matter whether there is the term "optionally" or not. Unless otherwise indicated, an "optionally substituted" group may have a suitable substituent at each substitutable position of the group, and when more than one position in a given structure can be substituted with more than one substituent selected from a specific group, the substituent at each position can be either the same or different. The substituents that can form stable or chemically feasible compounds are preferable. It also can be understood that, each substituent can be further optionally substituted (i.e., further substituted or unsubstituted), unless indicating otherwise.

The platinum complexes described herein can be prepared in accordance with a specific application, so as to meet the specific requirement on emission or absorption characteristic. The optical properties of the platinum complex according to the present disclosure can be modified by varying the structure of the ligand surrounding the metal center or varying the structure of fluorescent luminophore(s) on the ligands. For example, the platinum complex having a ligand with electron donating substituent or electron withdrawing substituent generally exhibits different optical properties, including emission and absorption spectra. The color of the platinum complex can be modified by changing conjugated groups of the fluorescent luminophores and ligands.

The emission of such complex can be modified by, for example, changing the structure of ligand or fluorescent luminophore (e.g., from the ultraviolet to near-infrared). A fluorescent luminophore is a group of atoms in an organic molecule that can absorb energy to generate a singlet excited state. The singlet exciton(s) produce(s) decay rapidly to yield prompt luminescence. In one aspect, the complex can provide emission over a majority of the visible spectrum. In a specific example, the complex described herein can emit light over a range of about 400 nm to about 700 nm. In another aspect, the complex improves the stability and efficiency of traditional emission complexes. In yet another aspect, the complex can be used as luminescent labels in, for example, biological application, anti-cancer agents, emitters in organic light emitting diodes (OLEDs), or combinations thereof. In another aspect, the complex can be used in light emitting devices, such as compact fluorescent lamps (CFL), light emitting diodes (LEDs), incandescent lamps, and the like.

The present disclosure provides a compound or compound complex containing platinum. The terms of compound, compound complex and complex are interchangeable in the present disclosure. In one aspect, the compound disclosed herein has a neutral charge.

The compounds disclosed herein can exhibit desirable properties and have emission and/or absorption spectra that can be modified by selecting appropriate ligands. In another aspect, any one or more of the compounds, structures, or portions thereof specifically described herein may be excluded.

The compound disclosed herein is applicable in a variety of optical and photoelectrical devices, including, but not limited to, light-absorbing devices such as solar- and light-sensitive devices, organic light-emitting diodes (OLEDs), light-emitting devices, devices capable of absorbing and emitting light, and biological markers.

As briefly described above, the disclosed compound is a platinum complex. In one aspect, the compound disclosed herein can be used in OLEDs, such as a host material of a full color display device.

The compounds disclosed herein can be used in a variety of applications. As luminescent materials, the compounds can be used in organic light emitting diodes (OLEDs), display devices, and other light-emitting devices.

In another aspect, these compounds can provide an improved efficiency and/or operational lifetimes in illumination devices, such as organic light-emitting devices, as compared to conventional materials.

Compounds described herein can be prepared by using a variety of methods, including, but not limited to those described in the examples.

The compounds disclosed herein include delayed fluorescent emitters, phosphorescent emitters, or combinations thereof. In one aspect, the compound disclosed herein is a delayed fluorescent emitters. In another aspect, the compound disclosed herein is a phosphorescent emitter. In yet another aspect, the compound disclosed herein is both a delayed fluorescent emitter and a phosphorescent emitter.

The present disclosure provides a metal platinum complex of Formula I (short for platinum complexes):

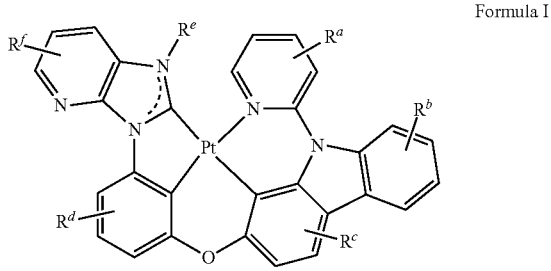

Formula I

Each of $R^a$ and $R^b$ can be hydrogen atom and its isotopes, respectively, and may be other monoatomic substituents (for example, deuterium or halogen); each of $R^a$ and $R^b$ also can be a substituent such as hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups; $R^a$ and $R^b$ may optionally bonded to form a ring.

Each of $R^c$ and $R^d$ is independently selected from hydrogen atom or a non-hydrogen atom. If each of $R^c$ and $R^d$ is selected from non-hydrogen atoms, each of $R^c$ and $R^d$ represents a substituent. Each of $R^c$ and $R^d$ is independently selected from deuterium, halogen, hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups.

Each of $R^e$ and $R^f$ is independently selected from alkyl groups, such as methyl, ethyl, isopropyl, isobutyl, tert-butyl; cyclopropyl or cyclobutyl; aryl groups, such as phenyl, 2-methylphenyl, 2,4-dimethylphenyl or 2,4,6-trimethylphenyl.

If $R^a$ and $R^b$ are optionally bonded to form a ring, the structures showed in formula II to formula V are obtained, where each of $R^a$, $R^c$, $R^d$, Re, Rf, $R^g$ and $R^h$ may independently be selected from alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, polymeric groups, or substituents containing isotopes. Further, if $R^a$ and $R^h$ are optionally bonded to form a ring, each of $R^b$, $R^c$, $R^d$, Rf and $R^g$ may also be a hydrogen atom or any other monoatomic substituent other than hydrogen ($^1H$) atom.

The platinum complex according to the present disclosure has a structure represented by complex 101, complex 102, complex 103, or complex 104.

Each of $R^b$, $R^c$, $R^d$ and Rf is independently selected deuterium, halogen, hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups; $R^a$ and $R^b$ may optionally be joined to form a fused ring.

The species of formula 101 to formula 104 are defined as below.

$R^a$ may represent mono-, di-, tri- or tetra-substitutions.

In one aspect, $R^a$ is independently selected from deuterium, $CDH_2$, $CD_2H$, $CD_3$, $CDR^1R^2$, $CD^2R^1$, and each of $R^1$ and $R^2$ is independently selected from alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester, alkoxycarbonyl, acylamino, alkoxycarbonylamino, aryloxycarbonylamino, sulfamoyl, carbamoyl, alkylthio, ureido, phosphoramide group, silyl, or polymeric groups.

In one aspect, $R^b$ is an atom or a substituent other than hydrogen. In another aspect, $R^b$ is hydrogen.

$R^b$ may represent mono-, di-, tri- or tetra-substitutions.

In one aspect, $R^b$ may be independently selected from deuterium, halogen, hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups.

In one aspect, $R^c$ is a substituent other than hydrogen. In another aspect, $R^c$ is hydrogen.

$R^c$ may represent mono-, or di-substitutions.

In one aspect, $R^c$ may be independently selected from deuterium, halogen, hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups.

In one aspect, $R^d$ is a substituent other than hydrogen. In another aspect, $R^d$ is hydrogen.

$R^d$ may represent mono-, di-, or tri-substitutions.

In one aspect, $R^d$ may be independently selected from deuterium, halogen, hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups.

In one aspect, $R^e$ is an independent substituent and may be alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups.

In one aspect, $R^f$ is a substituent other than hydrogen. In another aspect, $R^f$ is hydrogen.

In one aspect, $R^f$ may be independently selected from deuterium, halogen, hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester, alkoxycarbonyl, acylamino, alkoxycarbonylamino, aryloxycarbonylamino, sulfamoyl, carbamoyl, alkylthio, ureido, phosphoramide group, silyl, or polymeric groups.

In one aspect, $R^e$ is independently selected from alkyl-substituted alkyl, aryl-substituted alkyl, fluorine-substituted alkyl, aryl, alkyl-substituted aryl, aryl-substituted aryl, cycloalkyl, or alkyl or aryl substituted by other substituents.

From formula II to formula V, in one aspect, $R^h$ is a substituent other than hydrogen; in another aspect, $R^h$ is hydrogen.

In one aspect, each $R^h$ may be independently selected from deuterium, halogen, hydroxyl, hydrosulfuryl, nitro, cyano, isocyano, sulphinyl, sulphonyl, carboxyl, hydrazine; or alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups.

In one aspect, as regards any formula disclosed herein,

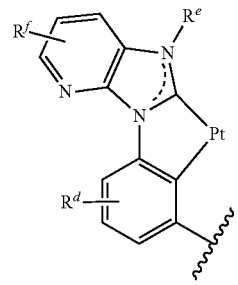

may be independently selected from one of the following structures. In another aspect, other structures or moieties that are not specifically described herein can be included, and the present disclosure is not intended to be limited to those structures or moieties that are specifically described.

Here are some exemplary fragments of platinum complexes:

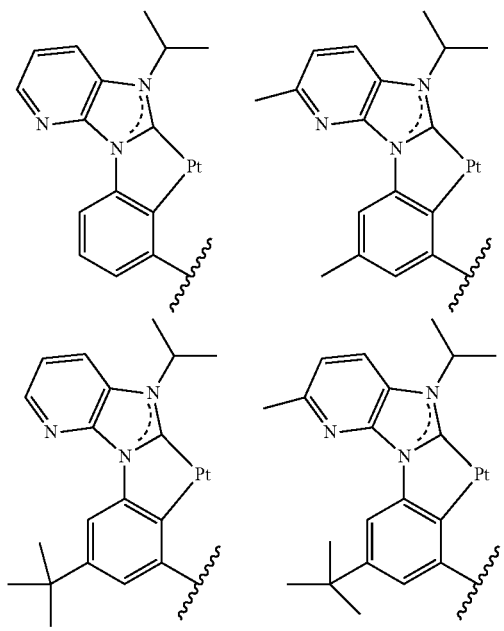

-continued

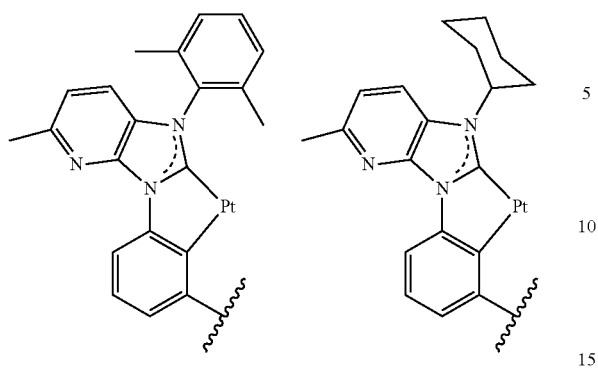

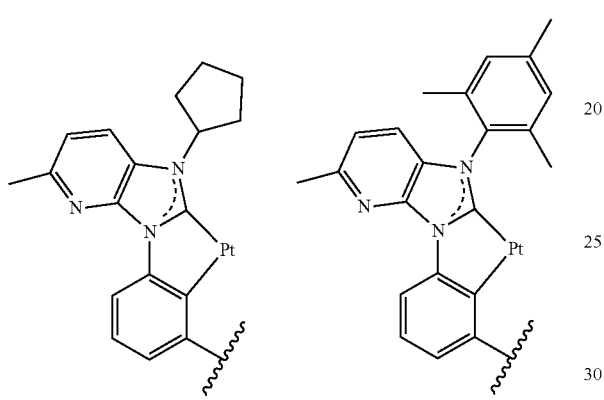

In one aspect, the platinum complex described in the present disclosure may include one or more of the following structures. It should be noted that $R^a$, $R^c$, $R^d$, $R^e$, $R^f$ and $R^g$ exist in a form of substituent. In the other aspect, they may also include other structures or moieties of these structures that are not explicitly mentioned herein, and disclosure of the present disclosure are not intended to limit to those structures or moieties thereof.

Complex 1

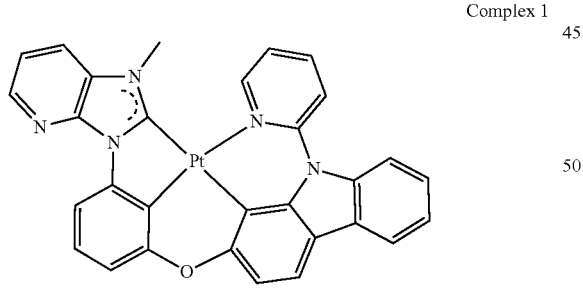

Complex 2

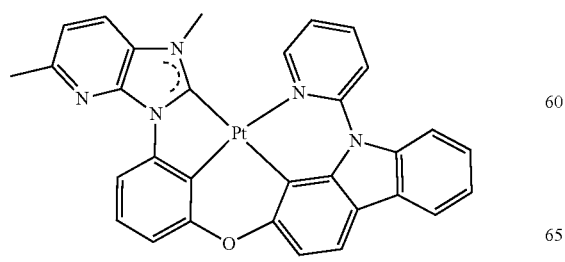

-continued

Complex 3

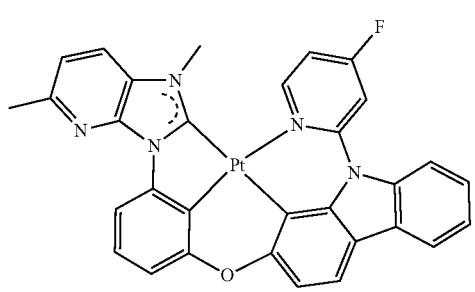

Complex 4

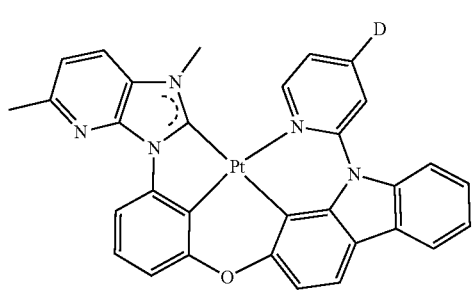

Complex 5

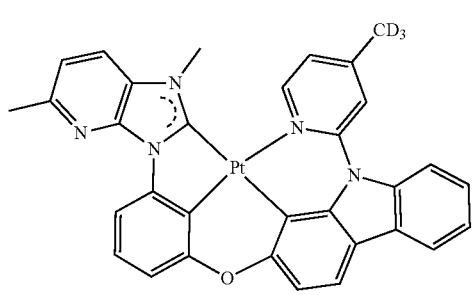

Complex 6

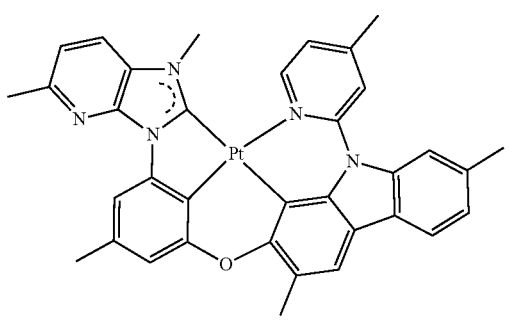

Complex 7

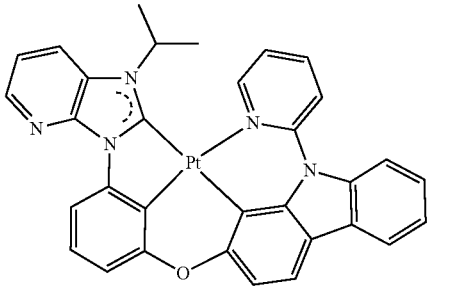

Complex 8
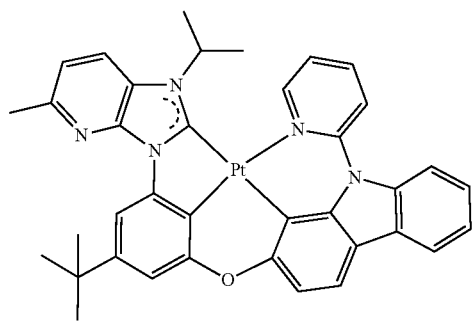
Complex 9
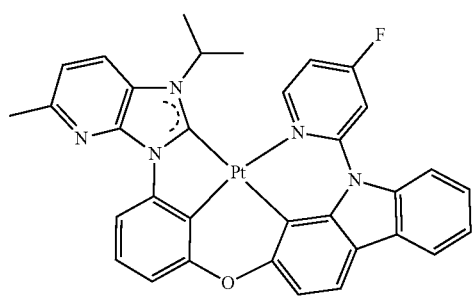
Complex 10
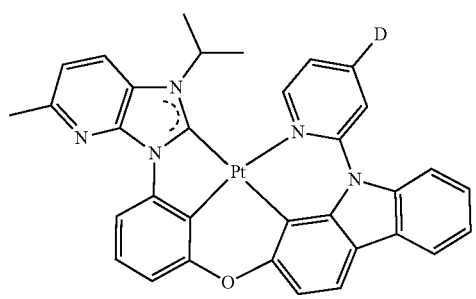
Complex 11
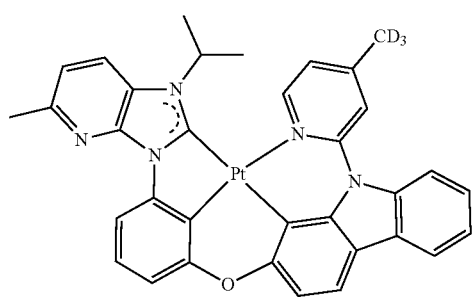
Complex 12
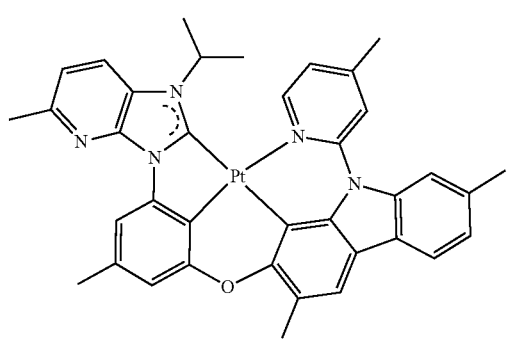
Complex 13
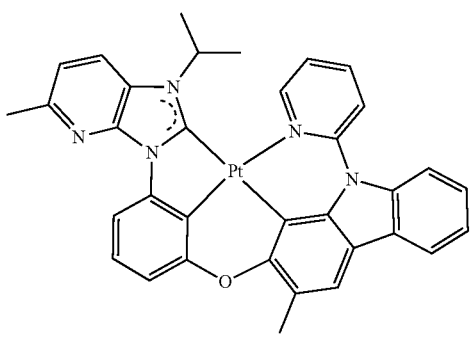
Complex 14
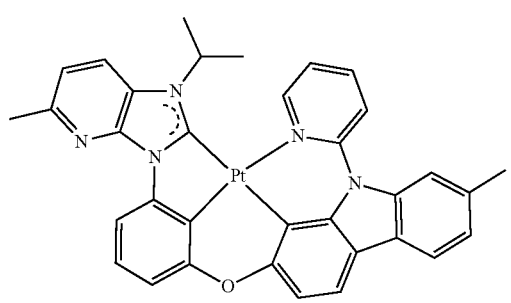
Complex 15
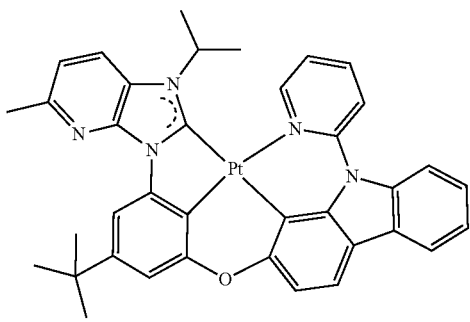
Complex 16
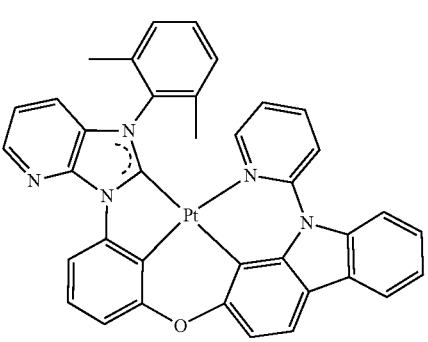

Complex 17
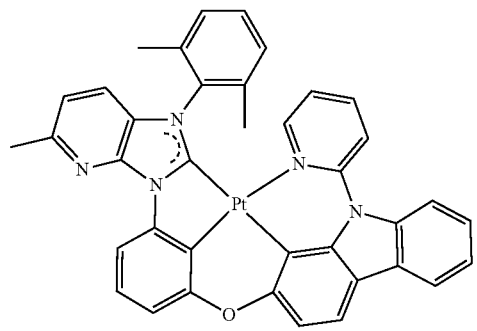
Complex 18
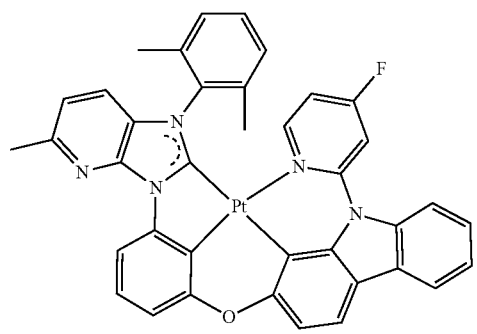
Complex 19
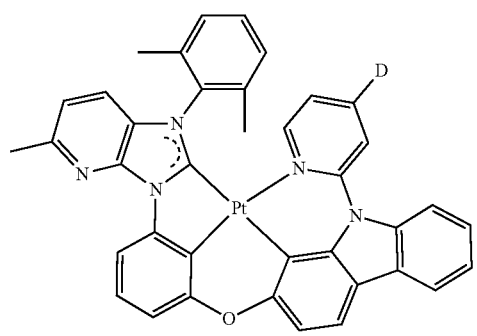
Complex 20
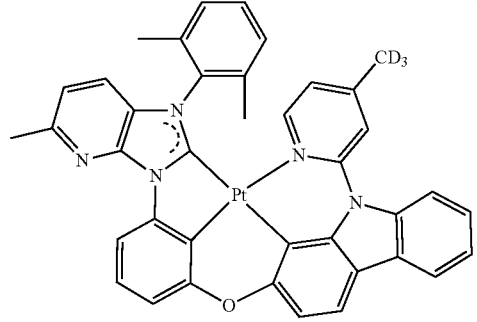
Complex 21
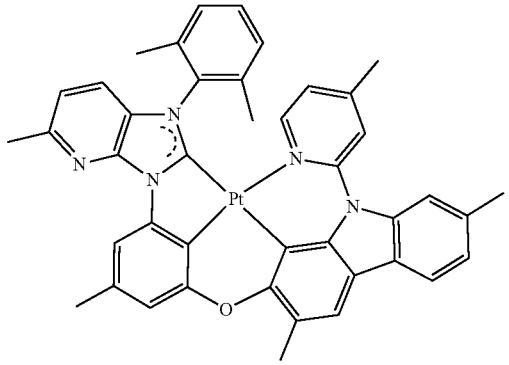
Complex 22
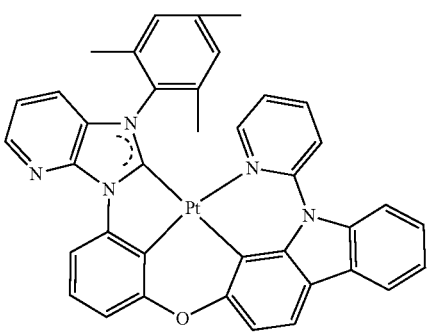
Complex 23
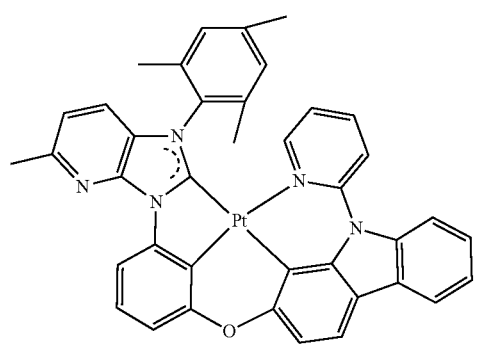
Complex 24
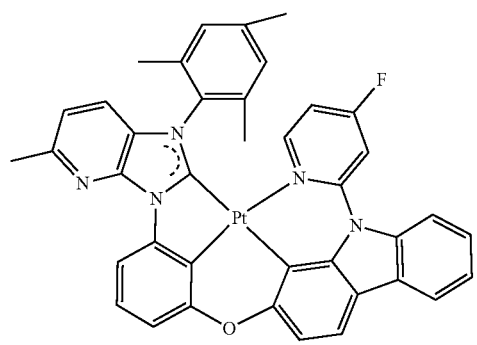

Complex 25
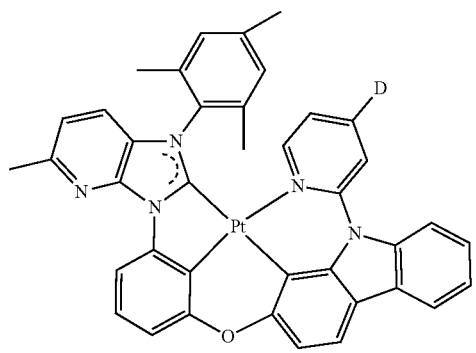
Complex 29
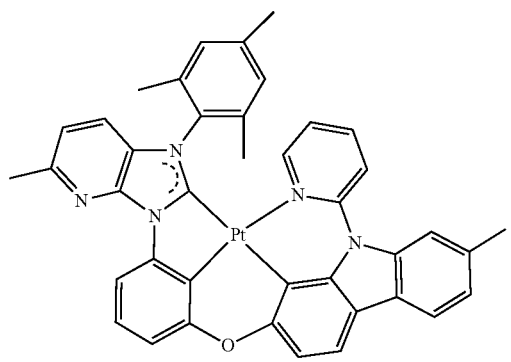
Complex 26
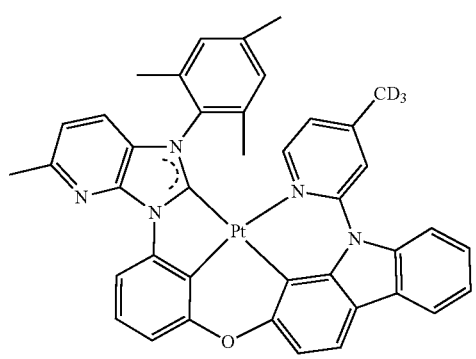
Complex 30
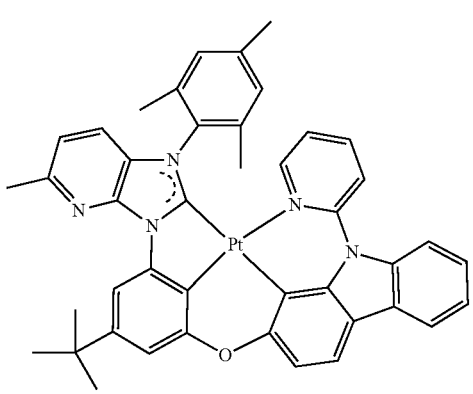
Complex 27
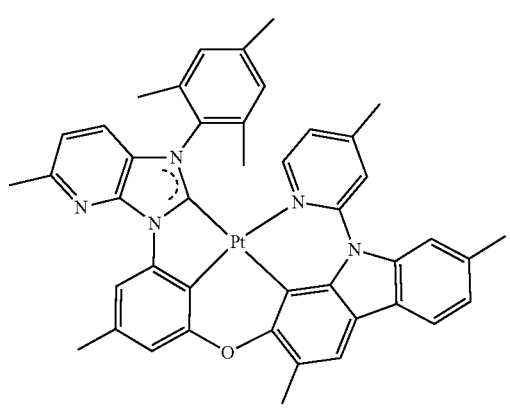
Complex 101
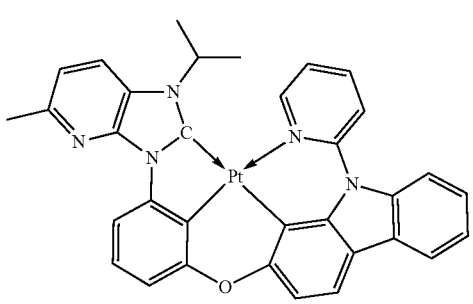
Complex 28
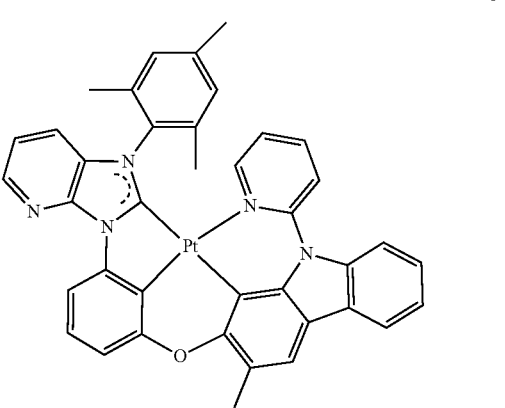
Complex 102
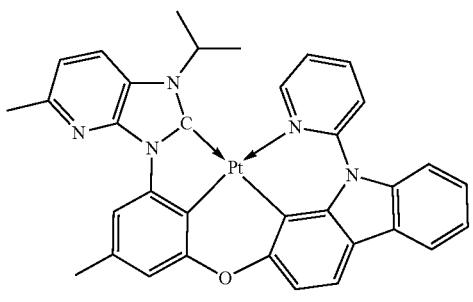

Complex 103

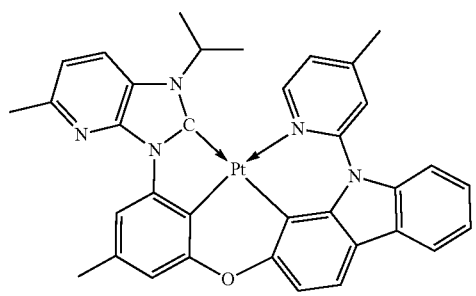

Complex 104

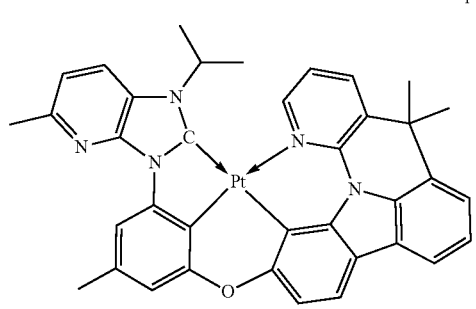

The present disclosure also provides a device including one or more of the platinum complexes disclosed herein, indicating that this material can be used in related optical and photoelectrical devices. The platinum complexes disclosed herein are applicable in a wide variety of optical and photoelectrical devices, including but not limited to light-absorption devices such as solar- and light-sensitive devices, organic light-emitting diodes (OLEDs), light-emitting devices, or devices capable of both absorbing and emitting light and biological markers.

The following examples are put forth so as to provide those skilled in the art with a complete disclosure and description of how the compounds, compositions, articles, devices and/or methods claimed herein are made and evaluated, and are intended to be purely exemplary, but not intended to be limiting in scope. Efforts have been made to ensure accuracy with respect to data (e.g., amounts, temperature, etc.), but some errors and deviations should be accounted for. Unless indicated otherwise, parts are weighted, temperature is in ° C. or is at ambient temperature, and pressure is at or near atmospheric pressure.

Various methods for the preparation of the compounds described herein are described in the examples. These methods are provided to illustrate various methods of preparation, but are not intended to limit any of the methods described herein. Accordingly, those skilled in the art in possession of this disclosure could readily modify a described method or utilize a different method to prepare one or more of the compounds described herein. The following aspects are only exemplary and are not intended to limit the scope of the present disclosure. Temperatures, catalysts, concentrations, reactant compositions, and other process conditions can vary, and those skilled in the art, in possession of this disclosure, could readily select appropriate reactants and conditions for a desired complex.

$^1$H-NMR (Hydrogen Nuclear Magnetic Resonance) and $^{13}$C-NMR (Carbon Nuclear Magnetic Resonance) spectra were recorded at 300, 400 or 500 MHz on Varian Liquid-State NMR instruments in CDCl$_3$ or DMSO-d$_6$ solutions and chemical shifts were referenced to residual protonated solvent. If CDCl$_3$ was used as solvent, $^1$H-NMR (Hydrogen Nuclear Magnetic Resonance) spectra were recorded with tetramethylsilane ($\delta$=0.00 ppm) as internal reference; $^{13}$C-NMR spectra were recorded with CDCl$_3$ ($\delta$=77.00 ppm) as internal reference. If DMSO-d$_6$ was used as solvent, $^1$H NMR (Hydrogen Nuclear Magnetic Resonance) spectra were recorded with residual H$_2$O ($\delta$=3.33 ppm) as internal reference; $^{13}$C-NMR (Carbon Nuclear Magnetic Resonance) spectra were recorded with DMSO-d$_6$ ($\delta$=39.52 ppm) as internal reference. The following abbreviations were used to explain multiplicity of $^1$H NMR (Hydrogen Nuclear Magnetic Resonance): s=singlet, d=doublet, t=triplet, q=quartet, p=quintet, m=multiplet, br=broad.

The present disclosure describes the properties of these platinum complexes and their properties as luminescent materials by taking complex 101, complex 102, complex 103 and complex 104 as examples.

Complex 101

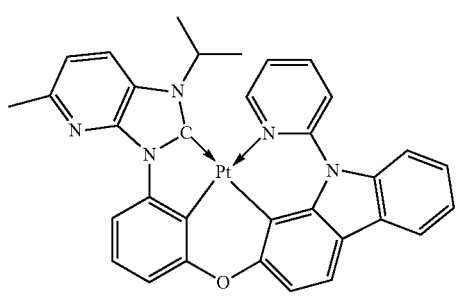

Complex 102

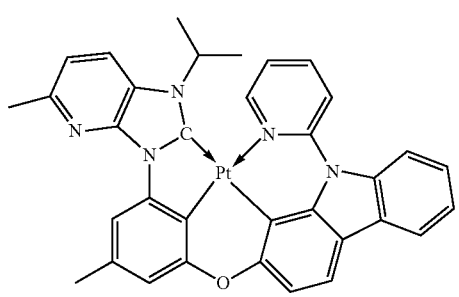

Complex 103

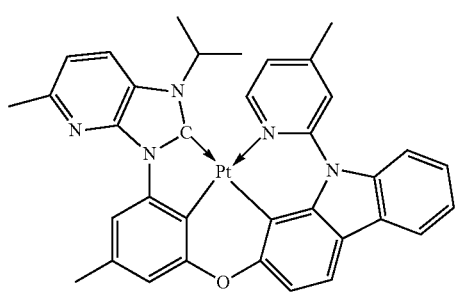

31
-continued

Complex 104

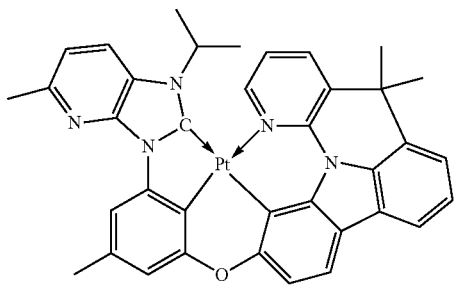

Example 1

Complex 102 and its preparation

Synthesis of 2-bromo-9-(2-pyridyl) carbazole 4101

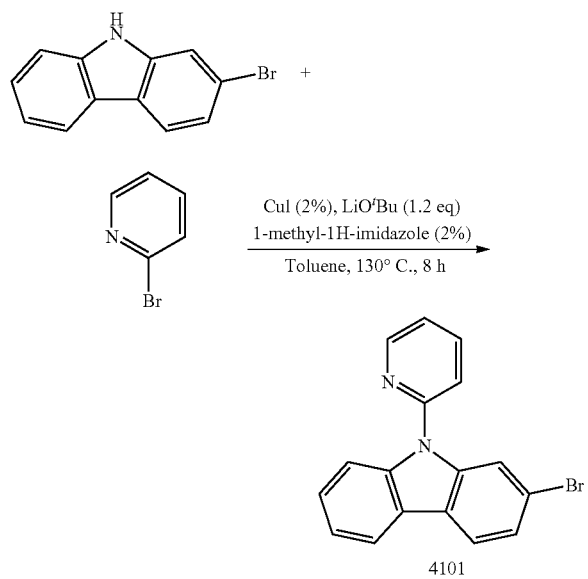

2-bromocarbazole (3.69 g, 15 mmol), 2-bromopyridine (1.57 mL, 16.5 mmol), cuprous iodide (0.3 mmL, 0.02 equiv), 1-methylimidazole (0.3 mmol, 1.2 equiv), t-BuOLi (18 mmol, 1.2 equiv) and toluene (50 mL) were added to a 48 mL sealed tube with a magnetic rotor, and the obtained mixture was bubbled with nitrogen for 10 min, then heated to 120° C. and stirred for 8 hours. After being cooled to room temperature, the reaction was quenched with water and extracted with ethyl acetate. The organic phases were combined, washed with saturated sodium chloride aqueous solution, and dried over anhydrous sodium sulfate. The solvent was removed by distillation under reduced pressure, and the obtained crude product was purified through silica gel column chromatography using petroleum ether: ethyl acetate=25:1 as eluent to give a white solid in a yield of 93%.

32

Synthesis of 2-(3-amino-5-methylphenol)-9-(2-pyridyl)carbazole 4103

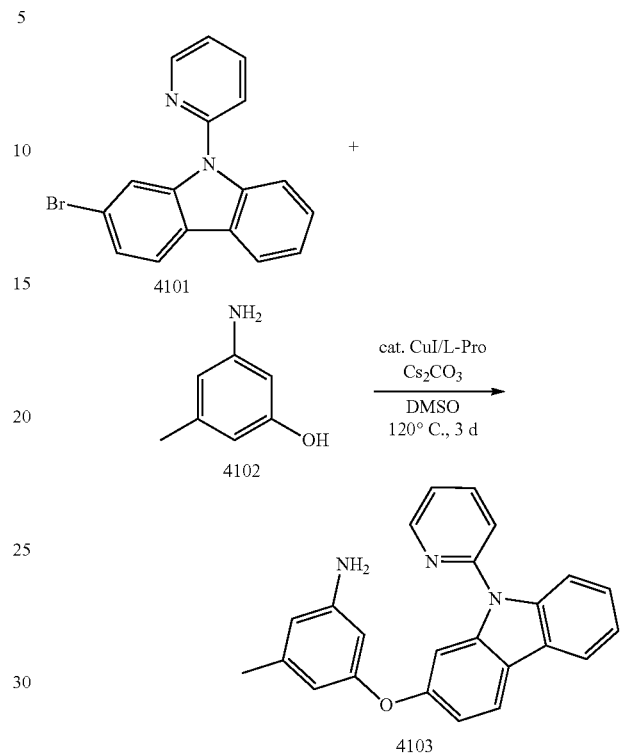

2-bromo-9-(2-pyridyl)carbazole 4101 (1 equiv), 3-amino-5-methylphenol 4102 (1.2 equiv), cuprous iodide (10%), L-proline (L-Pro, 20%), cesium carbonate (2 equiv) and dimethyl sulfoxide (0.5M) were added to a 25 ml Shrek tube. The obtained mixture was bubbled with nitrogen for 10 min and stirred 3 days at 120° C. After being cooled, water and ethyl acetate (EA) were added, and the mixture was filtered. The aqueous phase was extracted with ethyl acetate, and the respective organic phases were combined, washed with brine, dried over anhydrous $Na_2SO_4$. Then, the obtained solution was purified through silica gel chromatography using PE:EA=8:1 as eluent to give a target product 4103 (yellow viscous liquid, yield 75%). $^1$H-NMR (300 MHz, DMSO-$d_6$) δ 8.70 (dd, J=4.9, 1.9 Hz, 1H), 8.20 (dd, J=8.1, 5.0 Hz, 2H), 8.10 (td, J=7.8, 2.0 Hz, 1H), 7.76 (d, J=8.1 Hz, 2H), 7.50-7.39 (m, 3H), 7.32 (t, J=7.4 Hz, 1H), 6.98 (dd, J=8.5, 2.1 Hz, 1H), 6.12 (s, 1H), 5.99 (d, J=1.6 Hz, 2H), 2.11 (s, 3H).

Synthesis of 2-chloro-3-(isopropylamino)-6-methylpyridine (4105)

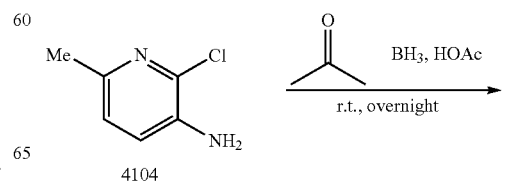

-continued

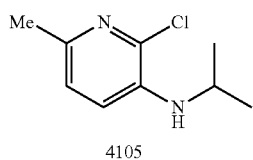
4105

15 ml of acetone and 75 ml of acetic acid were added into a solution of 8 g 3-amino-2-chloro-6-methylpyridine 4104 in 150 ml of methylene chloride. 6 ml of borane dimethylsulfide ether was added at 0° C., followed by stirring at room temperature overnight. After the reaction was completed, the solution was adjusted to pH 8 by adding 25 wt % aqueous ammonia solution. After adding 50 ml of water, extraction was performed three times with dichloromethane. The organic phases were collected, dried over anhydrous sodium sulfate, and dried by rotary evaporation to give a crude product of compound 4105, which was used directly in a next step (yellow oil, yield 95%).

Synthesis of pyridinediamine derivative 4106

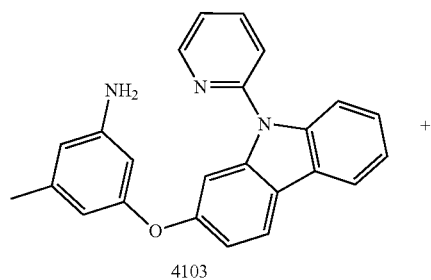
4103

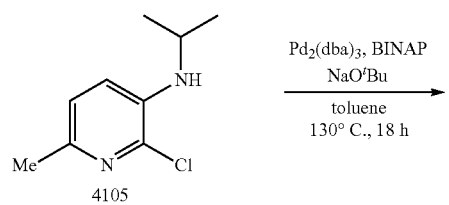
4105

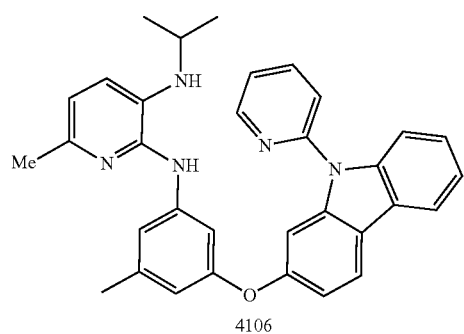
4106

2-chloro-3-(isopropylamino)-6-methylpyridine 4105 (1 equiv), 2-(3-amino-5-methylphenolyl)-9-(2-pyridyl) carbazole 4103 (1.1 equiv), tri(dibenzylidene acetone)dipalladium (5%), BINAP ((±)-2,2'-bis (diphenyl phosphino)-1,1'-binaphthyl, 5%), sodium tert-butoxide (1.5 equiv) and toluene (0.2 M) were added to a sealed tube in the glove box. The mixture was bubbled for 15 minutes and then heated at 130° C. for 18 hours. After being cooled, ethyl acetate was added and the mixture was filtered. The aqueous phase was extracted with ethyl acetate, the organic phases were mixed, washed with brine, and dried over anhydrous $Na_2SO_4$. The obtained solution was purified through silica gel chromatography using PE:EA=6:1 as eluent, and the eluent was dried by rotary evaporation to give the target product 4106 (yellow viscous liquid, yield 80%).

Synthesis of carbene hexafluorophosphate 4107

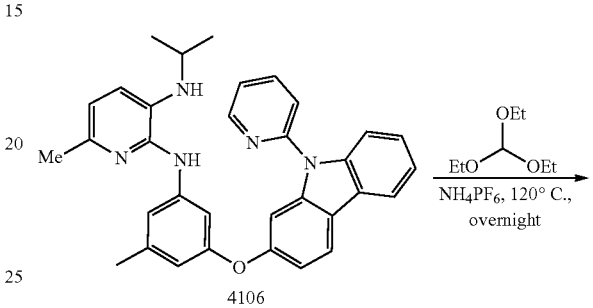
4106

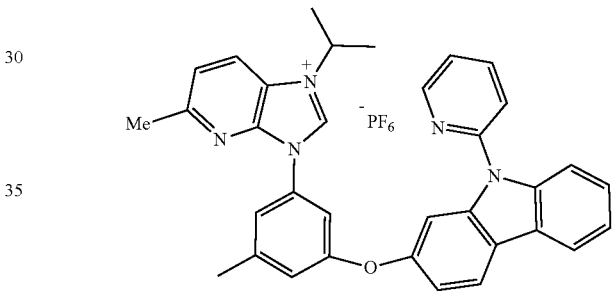
4107

Pyridinediamine derivative 4106 (1 equiv), ammonium hexafluorophosphate (1.1 equiv) and triethyl orthoformate (0.5 M) were added to a sealed tube. The obtained mixture was heated overnight at 120° C. After being cooled to room temperature, ethyl acetate was added to precipitate a yellow precipitate, which was filtered to obtain a product 4107 (yellow solid, yield 60%).

Synthesis of Complex 102

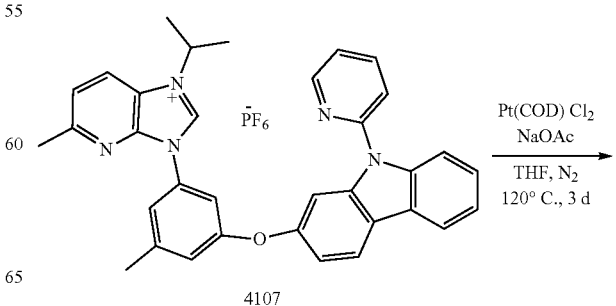
4107

35

-continued

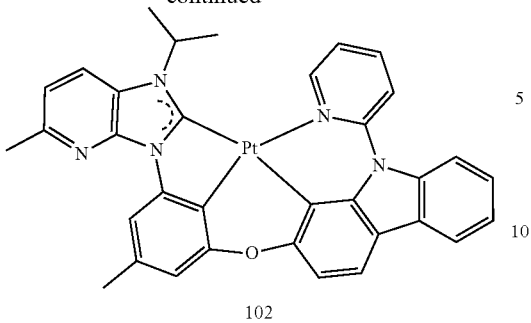

102

Carbene hexafluorophosphate 4107 (1 equiv), dichloro (1,5-cyclooctadiene) platinum (II) (Pt(COD)Cl2, 0.9 equiv), sodium acetate (1.05 equiv) and THF (0.5 M) were added to a sealed tube. The obtained mixture was heated at 120° C. for 3 days. After being cooled to room temperature, the mixture was dried by rotary evaporation, and the obtained solution was purified through silica gel chromatography using DCM:PE=4:1 as eluent to give target product: compound 102 (bright yellow powder, yield 38%). $^1$H-NMR (300 MHz, DMSO-$d_6$) δ 9.51 (d, J=6.2 Hz, 1H), 8.35 (d, J=8.3 Hz, 1H), 8.30 (s, 1H), 8.25-8.17 (m, 2H), 8.17-8.13 (m, 1H), 8.09 (d, J=8.0 Hz, 1H), 7.90 (d, J=8.3 Hz, 1H), 7.47 (t, J=7.6 Hz, 1H), 7.41 (d, J=7.5 Hz, 1H), 7.32 (d, J=8.3 Hz, 1H), 7.26 (d, J=8.4 Hz, 2H), 6.83 (s, 1H), 5.16 (p, J=7.0 Hz, 1H), 2.70 (s, 3H), 2.42 (s, 3H), 1.88 (d, J=6.8 Hz, 3H), 1.46 (d, J=6.7 Hz, 3H). MS (ESI): 717.2 [M+H$^+$].

Example 2

Complex 103 and its preparation 2-bromo-9-(4-methylpyridin-2-yl)carbazole 4203

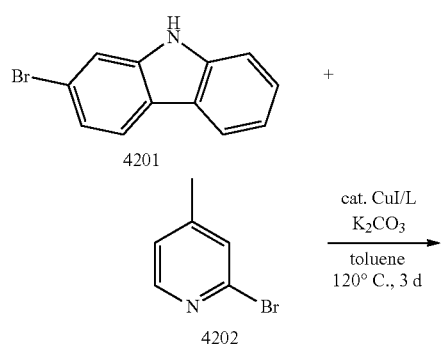

2-bromo-9-(4-methylpyridine-2-yl)carbazole 4203 was synthesized using a same method for 2-bromo-9-(2-pyridyl) carbazole, but 2-bromopyridine was replaced with 4-methyl-2-bromopyridine 4201 (light brown solid was used directly in the next step).

Synthesis of 2-(3-amino-5-methylphenol)-9-(4-methylpyridin-2-yl)carbazole 4205

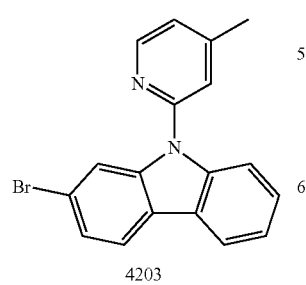

2-(3-amino-5-methylphenol)-9-(4-methylpyridin-2-yl) carbazole 4205 was synthesized using a same method for 2-(3-amino-5-methylphenol)-9-(2-pyridyl)carbazole 4103, but 2-bromo-9-(2-pyridyl)carbazole 4101 was replaced with 2-bromo-9-(4-methylpyridin-2-yl)carbazole 4203 to give the target product 4205 (cyan foamy substance, yield 76%).

Synthesis of pyridinediamine Derivative 4206

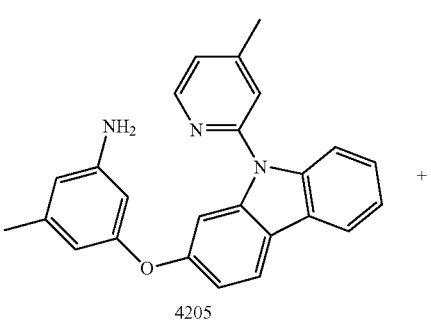

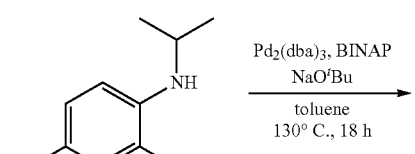

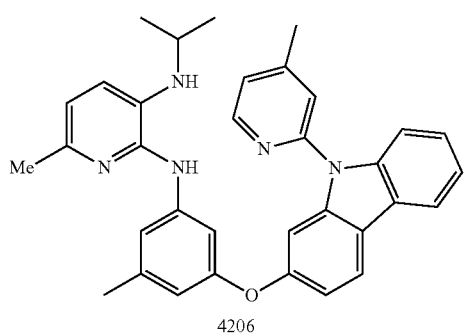

4206

Pyridinodiamine derivative 4206 was synthesized using a same method for pyridinediamine derivative 4106, but 2-(3-amino-5-methylphenol)-9-(2-pyridyl)carbazole 4103 was replaced with 2-(3-amino-5-methylphenol)-9-(4-methyl-pyridin-2-yl)carbazole 4205 to give the target product 4206 (bluish yellow foam, yield 80%).

Synthesis of carbene hexafluorophosphate 4207

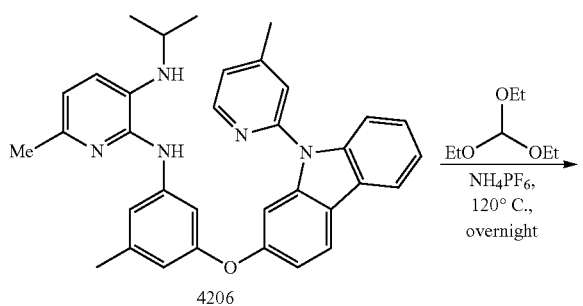

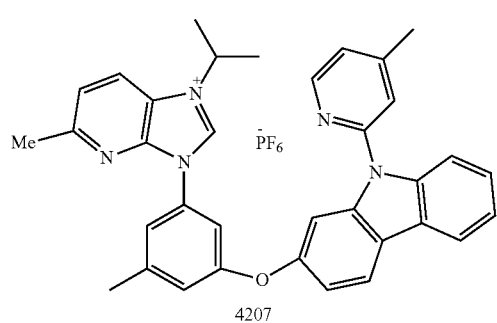

4207

Carbene hexafluorophosphate 4207 was synthesized using a same method for the synthesis of carbene hexafluorophosphate 4107, but the pyridinediamine derivative 4106 was replaced with pyridinediamine derivative 4206 to give the target product 4207 (dark yellow solid, 56% yield).

An alternative synthetic method for carbene hexafluorophosphate 4207 is provided: pyridinediamine derivative 4206 (1 equiv), ammonium iodide (1.05 equiv) and triethyl orthoformate (0.5 M) were added to a sealed tube; the obtained mixture was heated overnight at 120° C.; after being cooled to room temperature, ethyl acetate was added to precipitate a yellow precipitate; the yellow precipitate was filtered out to give a carbene iodide salt; the carbene iodide salt after being dried was dissolved with an appropriate amount of methanol, and ammonium hexafluorophosphate (1.05 equiv) was added; after adding an equal volume of water, the obtained mixture was stirred for 2 days; the solid was collected by filtration, washed with a small amount of ethyl acetate, giving a white solid 4207 (yield 60%).

Synthesis of Complex 103

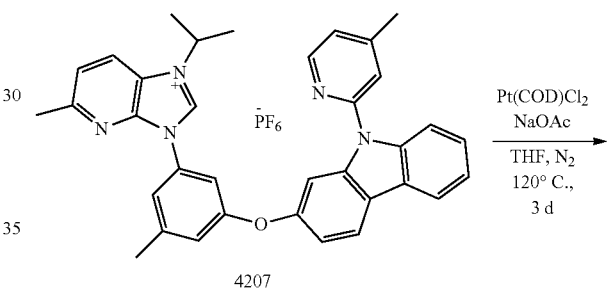

4207

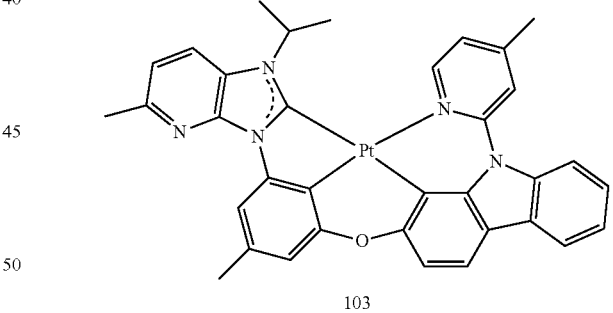

103

Complex 103 was synthesized by using a same method for the synthesis of complex 102, but carbene hexafluorophosphate 4107 was replaced with carbene hexafluorophosphate 4207 to give the target product 103 (yellow solid, yield 35%). $^1$H-NMR (300 MHz, DMSO-d$_6$) δ 9.35 (d, J=6.1 Hz, 1H), 8.40-8.27 (m, 2H), 8.14 (t, J=7.0 Hz, 2H), 8.02 (s, 1H), 7.89 (d, J=8.3 Hz, 1H), 7.48 (t, J=7.7 Hz, 1H), 7.40 (t, J=7.4 Hz, 1H), 7.33 (d, J=8.4 Hz, 1H), 7.24 (d, J=8.2 Hz, 1H), 7.14 (d, J=6.1 Hz, 1H), 6.82 (d, J=1.5 Hz, 1H), 5.26-5.10 (m, 1H), 2.70 (s, 3H), 2.42 (s, 6H), 1.90 (d, J=6.9 Hz, 3H), 1.47 (d, J=6.8 Hz, 3H). MS: 731.25 [M$^+$].

Example 3

Complex 101 and its preparation

Synthesis of 2-(3-aminophenol)-9-(2-pyridyl)carbazole 4303

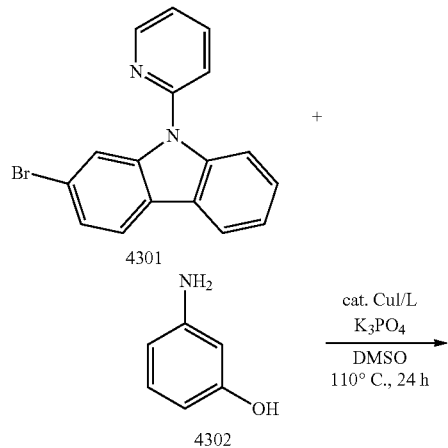

2-(3-aminophenol)-9-(2-pyridyl)carbazole was synthesized by using a same method for the synthesis of 2-(3-amino-5-methylphenol)-9-(2-pyridyl)carbazole 4103, but 3-amino-5-methylphenol 4102 was replaced with 3-aminophenol 4302 to give the target product 4303 (cyan foamy substance, yield 78%).

Synthesis of pyridinediamine derivative 4304

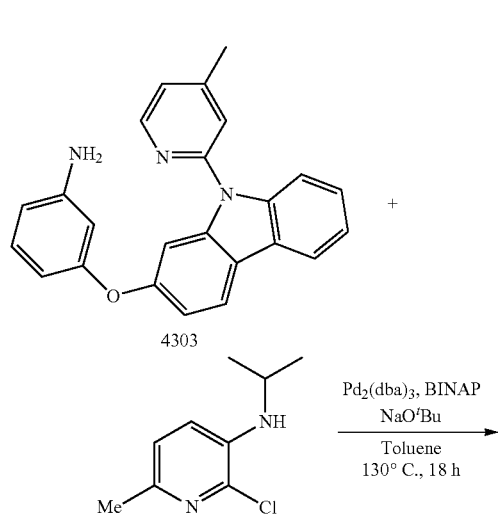

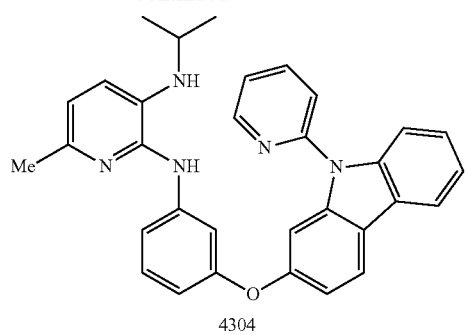

Pyridinediamine derivative 4304 was synthesized by using a same method for the synthesis of pyridinediamine derivative 4106, but 2-(3-amino-5-methylphenol)-9-(2-pyridyl)carbazole 4103 was replaced with 2-(3-amino-5-methylphenol)-9-(4-methylpyridin-2-yl)carbazole 4303 to give the target product 4304 (cyan foamy substance, yield 80%).

Synthesis of carbene hexafluorophosphate (4305)

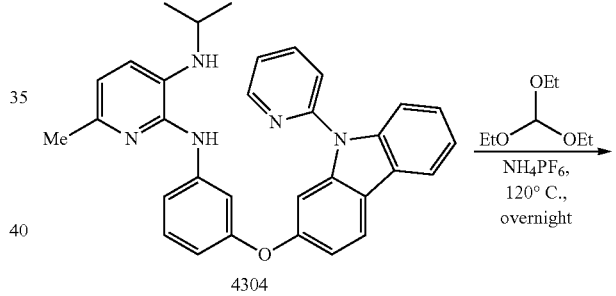

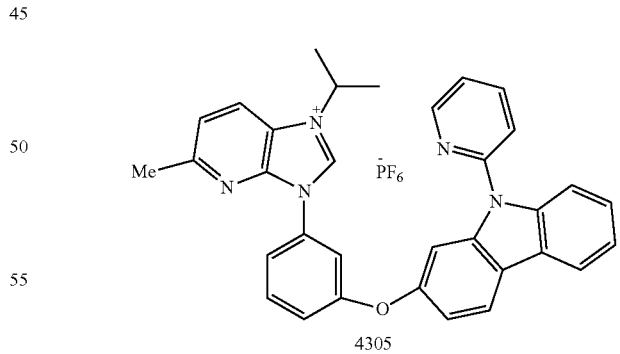

Carbene hexafluorophosphate 4305 was synthesized by using a same method for the synthesis of carbene hexafluorophosphate 4107, but the pyridinediamine derivative 4106 was replaced with pyridinediamine derivative 4304 to give the target product 4305 (dark yellow solid, yield 50%).

Synthesis of Complex 101

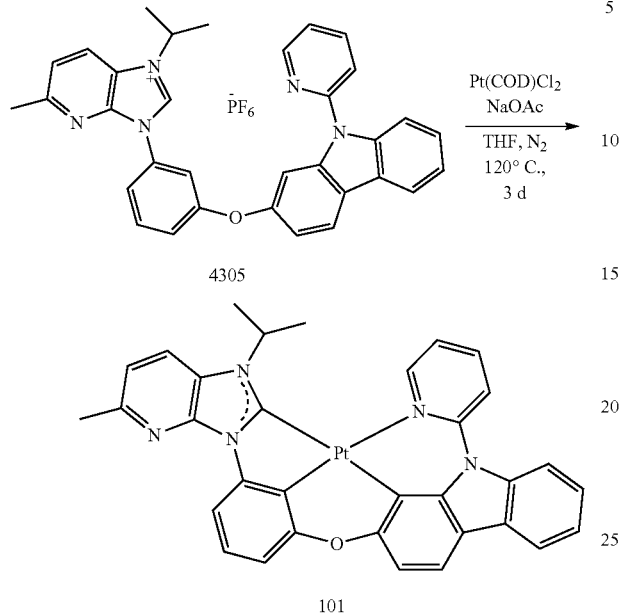

Complex 101 was synthesized by using a same method for the synthesis of complex 102, but the carbene hexafluorophosphate 4107 was replaced with carbene hexafluorophosphate 4305 to give the target product: complex 101 (yellow solid, yield 30%). $^1$H-NMR (300 MHz, DMSO-$d_6$) δ 9.53 (d, J=6.1 Hz, 1H), 8.47 (d, J=7.6 Hz, 1H), 8.37 (d, J=8.4 Hz, 1H), 8.23 (d, J=8.2 Hz, 2H), 8.14 (dd, J=15.7, 7.8 Hz, 2H), 7.92 (d, J=8.2 Hz, 1H), 7.58-7.25 (m, 6H), 6.99 (d, J=8.1 Hz, 1H), 5.25-5.09 (m, 1H), 2.70 (s, 3H), 1.90 (d, J=6.8 Hz, 3H), 1.48 (d, J=6.8 Hz, 3H). MS: 703.22 [M$^+$].

Example 4

Complex 104 and its preparation

Synthesis of 2-bromo-9-(3-methoxycarbonylpyridin-2-yl)carbazole (4402)

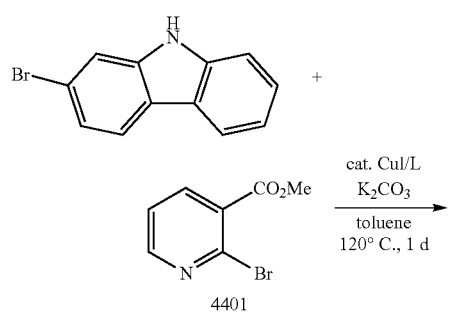

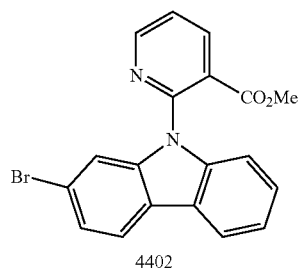

2-bromo-9-(3-methoxycarbonylpyridin-2-yl)carbazole 4402 was synthesized by using a same method for the synthesis of 2-bromo-9-(2-pyridyl)carbazole, but 2-bromopyridine is replaced with 4-methoxycarbonyl-2-bromopyridine 4401, the heating was carried out at 120° C. for 1 day to give the target product 4402 (light brown solid, used directly in the next step of reaction).

Synthesis of COMPOUND 4403

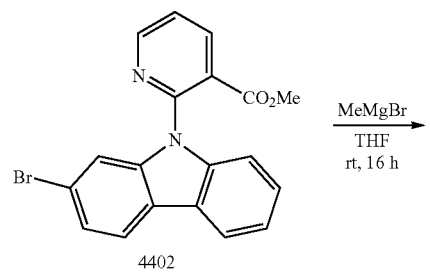

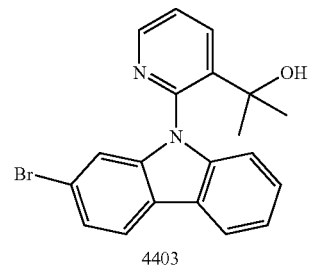

2-bromo-9-(3-methoxycarbonylpyridin-2-yl)carbazole 4402 (1 equiv), tetrahydrofuran (0.1 M) and tetrahydrofuran (0.1M) were added to a round bottom flask. A solution of methylmagnesium bromide in tetrahydrofuran (1 M, 4 equiv) was added dropwise, and the mixture was reacted at room temperature for 16 hours. After the reaction was completed, the reaction was quenched with saturated ammonium chloride, and the product was extracted with dichloromethane, and the organic phases were collected and dried over anhydrous sodium sulfate. The obtained solution was purified through silica gel chromatography using PE:EA=4:1 as eluent to give the target product 4403 (white solid, a total yield of 68% for two steps).

Synthesis of Compound 4404

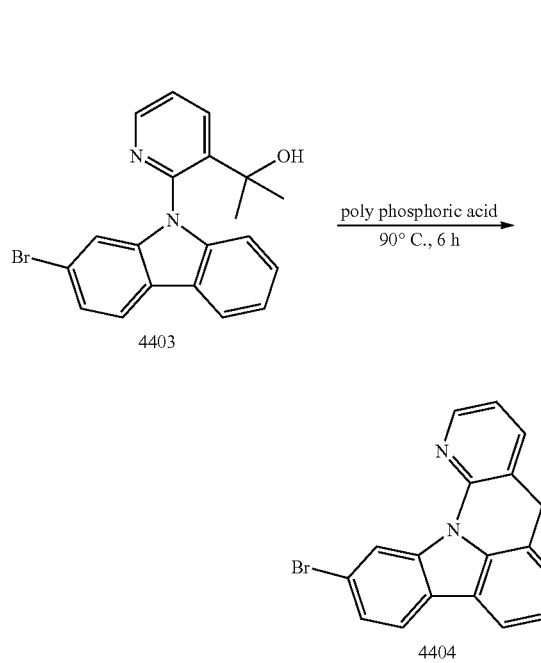

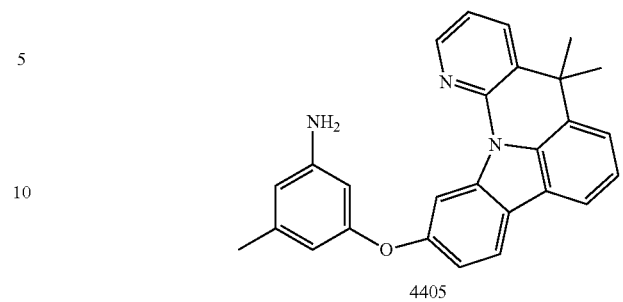

The product 4403 was added to a mixed solution (0.1M) of 98% concentrated sulfuric acid and polyphosphoric acid in a ratio of 1:1. The mixture was heated at 90° C. for 6 hours. After being cooled to room temperature, an appropriate amount of water was added and then a white precipitate was precipitated, and the aqueous phase was extracted with ethyl acetate, the organic phases were collected and dried over anhydrous sodium sulfate. After anhydrous sodium sulfate was filtrated, the filtrate was dried by rotary evaporation, and the solution was purified through silica gel chromatography by using PE:EA=5:1 as eluent to give the target product 4404 (yellow solid, yield 70%).

Synthesis of Compound 4405

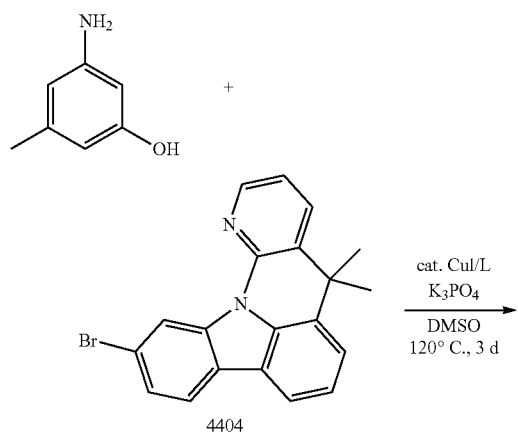

Compound 4405 was synthesized by using a same method for the synthesis of 2-(3-amino-5-methylphenol)-9-(2-pyridyl)carbazole 4103, but 2-bromo-9-(2-pyridyl)carbazole 4101 was replaced with 4404 to give the target product 4405 (brown foamy substance, yield 67%).

Synthesis of pyridinediamine Derivative 4406

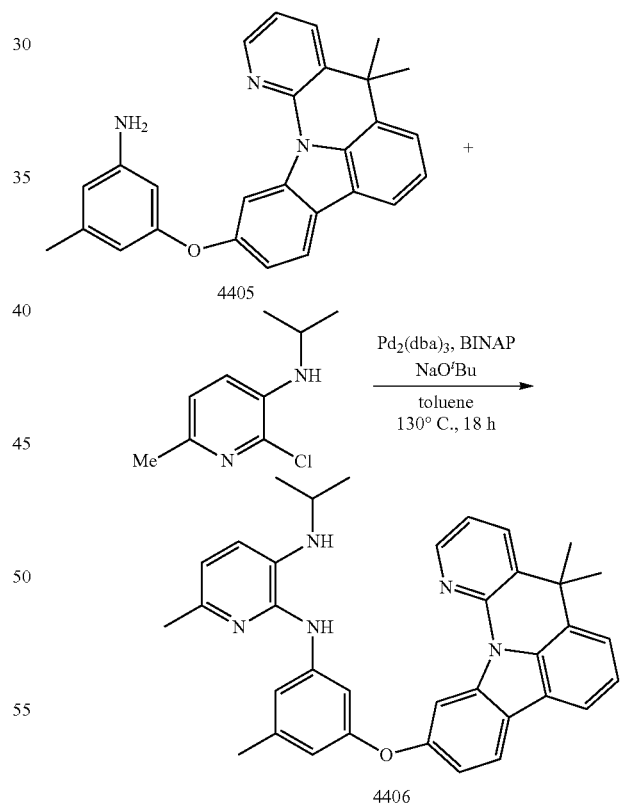

Pyridinediamine derivative 4406 was synthesized by using a same method for the synthesis of pyridinediamine derivative 4106, but 2-(3-amino-5-methylphenol)-9-(2-pyridyl)carbazole 4103 was replaced with the compound 4405 to give the target product 4406 (cyan foamy substance, yield 75%).

Synthesis of carbene hexafluorophosphate 4407

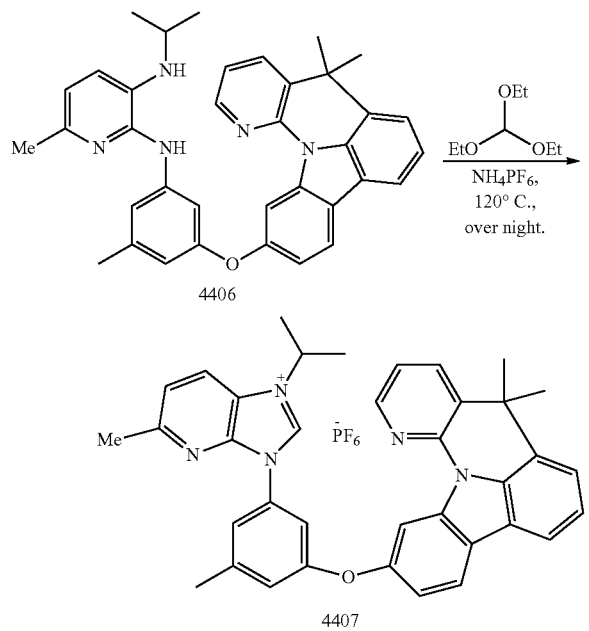

Carbene hexafluorophosphate 4407 was synthesized by using a same method for the synthesis of carbene hexafluorophosphate 4107, but the pyridinediamine derivative 4106 was replaced with pyridinediamine derivative 4406 to give the target product 4407 (brown solid, yield 58%).

Synthesis of Complex 104

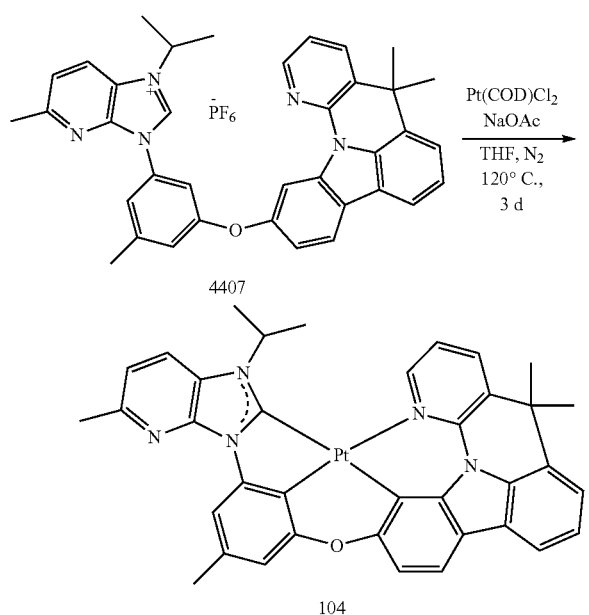

Complex 104 was synthesized by using a same method for the synthesis of complex 102, but carbene hexafluorophosphate 4107 was replaced with carbene hexafluorophosphate 4407 to give compound 104 as a bright yellow powder (yield 12%).

Example 5

Characterization Data of Platinum Complexes

The emission spectrum of the platinum complex of the present disclosure shows that the triplet energy gap is almost the same when a deuterium atom is added to the ligand.

Representative data for color purity of the emitter was obtained from the emission spectrum of a film prepared by using a solution of 5% PMMA (polymethyl methacrylate) in chloroform. As shown in Table 1, λ is a peak wavelength, FWHM is a full width at half maximum, and 450-700 nm is an integral proportion of the emission spectrum in a range of 450-500 nm, and CIE (x, y) is a chromaticity coordinate parameter according to the Standard from International Commission on Illumination. Each of the complexes 101-104 has a peak wavelength between 455 and 465 nm and full width at half maximum between 24-38 nm. The proportion of the spectrum within the range of 450-500 nm, which is visually healthy blue light emitting region, is above 70%. Moreover, the four platinum complex examples are all within the deep blue luminescent range (x<0.15, y<0.15), where complex 101 meets the standard for pure blue light material (X=0.14, Y=0.10). The properties of low energy and narrow spectrum prove that this class of platinum complexes can be used as extremely excellent blue light materials.

TABLE 1

| Complex | λ/nm | FWHM/nm | 450-500 nm/% | CIE (x, y) |
| --- | --- | --- | --- | --- |
| Complex 101 | 456 | 24 | 76.4 | 0.138, 0.104 |
| Complex 102 | 459 | 27 | 74.3 | 0.135, 0.132 |
| Complex 103 | 461 | 28 | 75.6 | 0.138, 0.136 |
| Complex 104 | 458 | 38 | 71.8 | 0.140, 0.142 |

Band gap and associated optical properties of the platinum complexes 101-104 in the present disclosure are characterized as follows: band gap value ($E_g$), and the LUMO and HOMO value were measured by using cyclic voltammetry (CV). The whole test process was carried out on the CHI600D electrochemical workstation (Shanghai Chenhua Instrument Co., Ltd.) in the glove box (Lab2000, Etelux), using a three-electrode system consisting of Pt column as working electrode, Ag/AgCl as reference electrode, and Pt wire as auxiliary electrode. The medium used in the test is a solution of 0.1M hexafluorophosphate tetrabutylammonium ($Bu_4NPF_6$) in dimethylformamide (DMF), and the potential was measured with reference to the added ferrocene (Fc) as an internal standard. In the Table shown as below, λ is a peak wavelength of the platinum complex dissolved in methylene chloride, FWHM is a full width at half maximum of the platinum complex, and the triplet photon energy of the material ($E_{T1}$) is calculated by the formula $1240/\lambda_{0\rightarrow 1}$ ($\lambda_{0\rightarrow 1}$ is the first vibration peak under 77 K) in electronic volt (eV). It can be seen from the data in Table 2 that the HOMO energy levels of the complexes 102, 103, and 104 are lower than the HOMO energy level of the complex 101, indicating that methylation on the phenyl group can increase the HOMO energy level of the material. The LUMO energy levels of complexes 101 and 102 are lower than the LUMO low levels of the complexes 103 and 104, indicating that introducing substituents on the pyridine can increase the LUMO energy level. The triplet energy of the four platinum complexes is uniformly 2.81 eV, which is mainly correlated to the core structure, indicating that the triplet radiation transitions are consistent under low temperature condition, i.e., a condition under which thermal motion of molecules is restricted. That is, these platinum complexes can be adjusted with respect to its energy level and its emission spectrum within a narrow range, by introducing a substituent, so as to obtain an optimal luminescence spectrum range.

TABLE 2

| Complex | $E_{HOMO}/$ eV | $E_{LUMO}/$ eV | Eg/ eV | λ/ nm | FWHM/ nm | $E_{T1}/$ eV | PLQY/ % |
|---|---|---|---|---|---|---|---|
| Complex 101 | −5.31 | −2.31 | 3.00 | 458 | 31 | 2.81 | 35 |
| Complex 102 | −5.29 | −2.30 | 2.99 | 463 | 38 | 2.81 | 57 |
| Complex 103 | −5.27 | −2.20 | 3.07 | 461 | 34 | 2.81 | 41 |
| Complex 104 | −5.28 | −2.17 | 3.11 | 464 | 46 | 2.81 | 27 |

Example 6

Preparation of OLED Light-Emitting Device and its Performance

Figure 8:
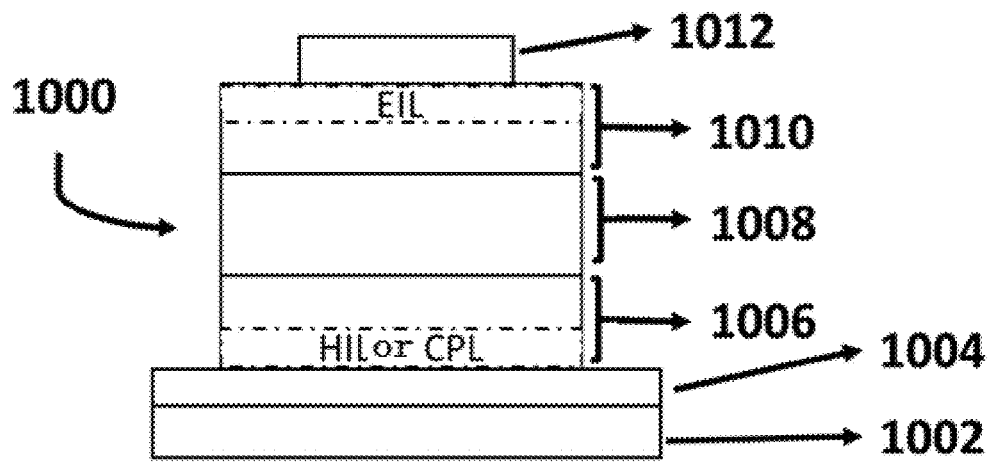
FIG. 8 shows a cross-sectional view of an OLED device 1000, where the OLED device includes one of the platinum complexes provided in the present disclosure—complex 101. The OLED device 1000 includes a substrate 1002, an anode layer 1004, a hole transmission layer 1006, a light-emitting layer 1008, an electron transmission layer 1010, and a metal cathode layer 1012. The anode 1004 is typically a transparent material such as indium tin oxide. The light-emitting layer 1008 can be a luminescent material including an emitter and a host. EIL refers to an electron injection layer, which can be regarded as a part of the electron transmission layer 1010. HIL is a hole injection layer, which can be regarded as a part of the hole transmission layer 1006. CPL is a cathode capping layer. The complex 101 disclosed herein is used as a blue luminescent dopant in the light-emitting layer 1008. When the complex 101 is used in an OLED device, the device is fabricated by spin coating, and has a structure as follows: ITO/PEDOT:PSS (70 nm)/MCP:complex 101 (95:5, 40 nm)/DPEPO (10 nm)/TmPyPB (50 nm)/Liq (1 nm)/Al (100 nm).
Figure 9:
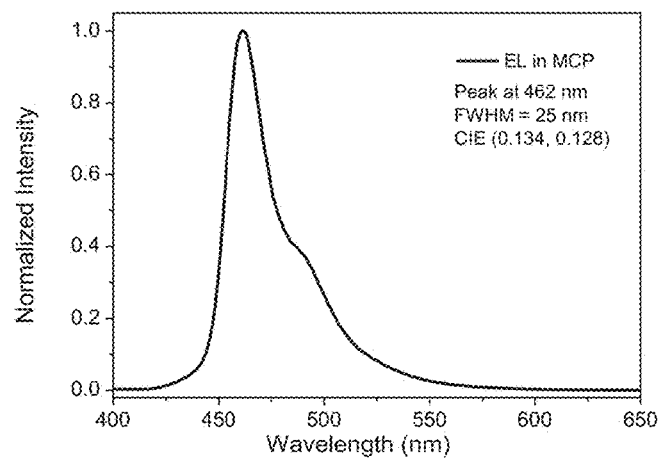
FIG. 9 shows an emission spectrum of an OLED device according to the present disclosure, which is an emission spectrum of the OLED having a structure of ITO/PEDOT:PSS (70 nm)/MCP:complex 101 (95:5, 40 nm)/DPEPO (10 nm)/TmPyPB (50 nm)/Liq (1 nm)/Al (100 nm). According to the electroluminescence spectrum of the device in which the light-emitting layer is doped with 5% of the complex 101, a luminescence peak is red-shifted by 6 nm with respect to its photoluminescence peak in a PMMA medium, and the full width at half maximum is comparable, thereby maintaining the luminescent characteristics of the complex 101. The calculated coordinate value of chromaticity is CIE (0.134, 0.128), which indicates that the device emits deep blue light.
Figure 10:
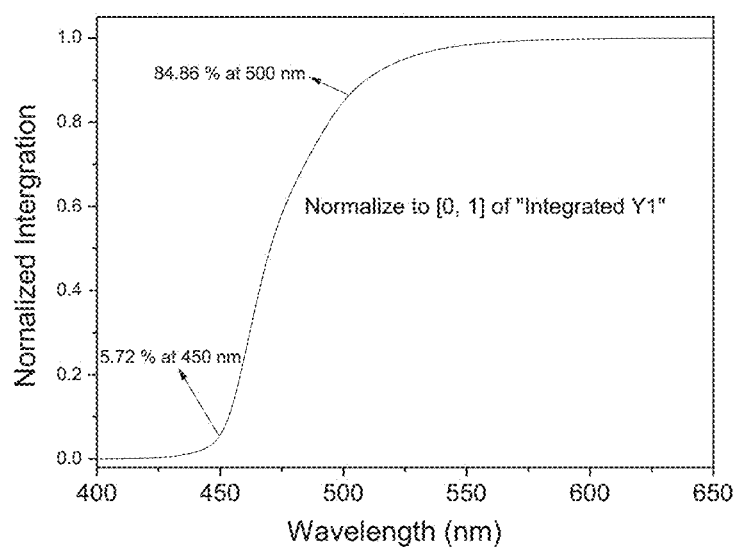
FIG. 10 shows a normalized integration schematic of an emission spectrum of the OLED having a structure of ITO/PEDOT:PSS (70 nm)/MCP:complex 101 (95:5, 40 nm)/DPEPO (10 nm)/TmPyPB (50 nm)/Liq (1 nm)/Al (100 nm) in electroluminescent spectral range of complex 101. According to the normalized integration, a proportion of an irritant blue light smaller than 450 nm is only 5.7%, and the energy of 84.9% photons is above 500 nm. According to the traditional blue light designation, the blue photons having wavelength in a range of 450-500 nm accounts for 79.1% of all emitted photons.
Figure 11:
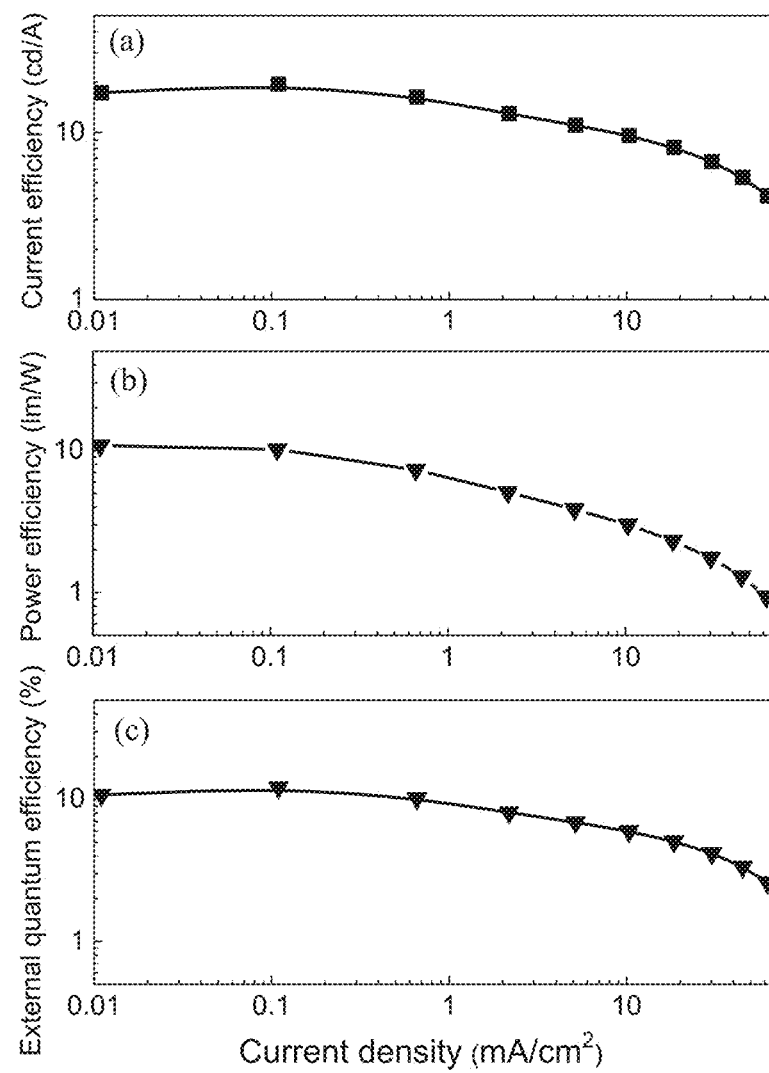
FIG. 11 shows a photoelectric conversion efficiency of a device containing complex 101, (a) current efficiency, (b)

FIG. 8 shows a sectional view of an OLED light-emitting device 1000, and the OLED light-emitting device 1000 includes: a substrate 1002 with an anode 1004, a hole transmission layer (HTL) 1006, a light-emitting layer 1008, an electron transmission layer (ETL) 1010 and a metal cathode layer 1012. The anode 1004 is typically a transparent material (e.g., indium tin oxide) and the light-emitting layer 1008 includes an emitter and a host luminescent material. The light-emitting device, such as an OLED, may include one or more light-emitting units. Any layer of the one or more light-emitting units may include indium tin oxide (ITO), MoO₃, Ni₂O₃, poly(3,4-ethylenedioxythiophene) (PEDOT), polystyrene sulfonate (PSS), 4,4',4"-((1E, 1'E,1"E)-cyclopropane-1,2,3-triylidenetris (cyano-methanylylidene))tris(2,3,5,6-tetrafluorobenzonitrile) (NHT-49), 2,2'-(perfluoro naphthalene-2,6-diylidene) dimalononitrile (NHT-51), 2,3,5,6-tetrafluorotetracyano-quinodimethane (F4-TCNQ), N,N'-di-1-naphthyl-N,N'-diphenyl-1,1'-biphenyl-4,4'diamine (NPD), 3,3'-bicarbazole structure (DMC-zMDP, BCzPO, BCzTPM, BCzPh). Referring to Literature 1: 3,3'-Bicarbazole-Based Host Materials for High-Efficiency Blue Phosphorescent OLEDs with Extremely Low Driving Voltage Hisahiro Sasabe, Naoki Toyota, Hiromi Nakanishi, Tasuku Ishizaka, Yong-Jin Pu and Junji Kido *Adv. Mater.* 2012, 24, 3212-3217, 1,1-cis((di-4-tolylamino) phenyl) cyclohexane (TAPC), 9,9'-(2,2'-dimethyl-[1, 1'-diphenyl]-4,4'-bi)bis (3,6-dimethyl-9H-carbazole) (DMC-ZMDP); Reference 2: A series of CBP-derivatives as host materials for blue phosphorescent organic light-emitting diodes Pamela Schrögel, Aušra Tomkevičien, Peter Strohriegl, Sebastian T. Hoffmann, Anna Köhlerb and Christian Lennartz. *J. Mater. Chem.*, 2011, 21, 2266-2273, 1,3-bis (carbazol-9-yl)benzene (mCP), 2,6-cis (N-carbazolyl)-pyridine (mCPy), 9-(4-tert-butylphenyl)-3,6-terphenyl sility-9H-carbazole (CzSi), 2,8-cis(diphenylphosphoryl)dibenzothiophene (PO15), bis[2-((oxo)diphenyl phosphino)phenyl] ether (DPEPO), phenylpyridine structures (1,3,5-tris[(3-pyridyl)-3-phenyl] benzene/TmPyPB, 1,3-bis [3,5-di(3-pyridyl)phenyl] benzene/BmPyPB), LiF, LiQ, Cs₂ CO₃, CaCO₃, Al or a combination thereof. In this embodiment, the light-emitting layer 1008 may include one or more platinum complexes according to the present disclosure, optionally together with a host material. The ETL layers 1010 and 1006 may also include one or more platinum complexes and another injection layer adjacent to the electrodes. The material of the injection layer may be included in an EIL (electron injection layer), a HIL (hole injection layer), and a CPL (cathode covering layer), which may be in a form of a single layer or dispersed in an electron or hole transmission material. The host material may be any suitable host material known in the art. The emission color of an OLED is determined by the emission energy (optical energy gap) of the material of the light-emitting layer 1008, and the emission energy (optical energy gap) of material of the light-emitting layer 1008 can be adjusted by modifying the electronic structure of the platinum complexes and/or the host material, as discussed above. Both the hole transmission material in the HTL 1006 and the electron transmission material in the ETL 1010 can include any suitable hole transmission known in the art.

Obviously, the platinum complexes according to the present disclosure can exhibit phosphorescence. Phosphorescent OLEDs (i.e., OLEDs with phosphorescent emitters) typically have higher device efficiency than other OLEDs, such as fluorescent OLEDs. Light-emitting devices based on electrophosphorescent emitters are described in Nature 1998, 395, 151-154, which is incorporated herein by reference due to its contents about OLED (in particular about phosphorescent OLEDs).

From various aspects, any of the one or more layers of 1006 illustrated in FIG. 8 may include indium tin oxide (ITO), MoO₃, Ni₂O₃, poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-cis(N-carbazolyl)pyridine (mCpy), 2,8-cis(diphenylphosphoryl) dibenzothiophene (PO15), LiF, Al, or combinations thereof.

The light-emitting layer 1008 may include one or more platinum complexes of the present disclosure optionally together with a host material. The host material may be any one known in the art. The emission color of an OLED is determined by the emission energy (optical energy gap) of the material of the light-emitting layer 1008, and the emission energy (optical energy gap) of material of the light-emitting layer 1008 can be adjusted by modifying the electronic structure of the emitting platinum complexes, the host material, or both of them. Both the hole transmission material in the HTL 1006 and the electron transmission material(s) in the ETL 1010 may include any suitable hole transmission material known in the art.

The platinum complexes described herein can exhibit phosphorescence. Phosphorescent OLEDs (i.e., OLEDs with phosphorescent emitters) typically have higher device efficiency than other OLEDs, such as fluorescent OLEDs. Light-emitting devices based on electrophosphorescent emitters are described in detail in WO2000/070655, which is incorporated herein by reference for its teaching of OLEDs, and in particular phosphorescent OLEDs.

An OLED light-emitting device having following structure was designed: ITO/PEDOT:PSS (70 nm)/MCP:Complex 101 (95:5, 40 nm)/DPEPO (10 nm)/TmPyPB (50 nm)/Liq (1 nm)/Al (100 nm). A crucible containing OLED organic material and a crucible containing metal aluminum particles were sequentially placed at an organic evaporation source and an inorganic evaporation source. The chamber was closed, and a primary evacuation and a high vacuum evacuation were performed so that the interior of the OLED evaporation apparatus reached a vacuum of $10E^{-7}$ Torr. Evaporation method for forming film of OLED is proceeded as follow: the OLED organic evaporation source was started, the OLED organic material was preheated at 100° C. for 15 minutes so as to further remove water vapor in OLED organic material; then, the organic material to be evaporated was subjected to a heating treatment by increasing temperature rapidly, and the baffle above the evaporation source was opened until organic material began coming out from the evaporation source of the material and the crystal oscillator detected an evaporation rate; slowly heated up with a temperature rise of 1-5° C. until the evaporation rate was stable at 1 A/sec; a baffle right under a mask was opened to form the OLED film; when the organic film on the ITO substrate was observed at the computer reaching a predetermined film thickness, both the baffle of the mask and the baffle over the evaporation source were closed; and the heater for the evaporation source of the organic material was turned off. The evaporation processes for other organic materials and cathode metal materials are described as above. Encapsulation was carried out by photo-curing encapsulation with UV epoxide resin. IVL performances of the encapsulated samples were tested by using Mc Science M6100. Test Data of the light-emitting devices are shown and compared in Table 3.

TABLE 3

| Complex | Peak Wavelength (nm) | chromaticity coordinate CIE (x, y) | EQE (1000 cd²A⁻¹) | PE lmW⁻¹ (1000 cd²A⁻¹) |
| --- | --- | --- | --- | --- |
| Complex 101 | 462 | (0.14, 0.14) | 9.5 | 13 |
| Complex 102 | 464 | (0.14, 0.17) | 14.2 | 22 |
| Complex 103 | 456 | (0.14, 0.15) | 12.7 | 17 |
| Complex 104 | 458 | (0.18, 0.27) | 7.7 | 10 |

As shown in Table 3, through comparing the data of the light-emitting devices, the electroluminescence wavelengths of the light-emitting devices are mainly determined by the photoluminescence of the platinum complex itself, and the purity of the photoluminescence spectrum of the platinum complex itself is directly correlated to the purity of the electroluminescence spectrum. Under the same condition, the efficiency of the light-emitting device is also consistent with the trend of the luminescence quantum efficiency of the platinum complex. The color purity of the light-emitting device is directly associated with the spectral color purity of the emitted light of the dopant material under optical excitation. By comparing the electroluminescence spectrum of the light-emitting device containing the platinum complexes with the photoluminescence device in the film, the electroluminescence spectrum of the light-emitting device is slightly red-shifted compared with the film photoluminescence spectrum, but the peak wavelength is still within the blue light region (460-470 nm), most of the spectrum is also within the blue light range, and the calculated chromaticity coordinates indicate that the light-emitting device is a pure blue light-emitting device. Since most of the light is in the blue light range and only a small amount of long wavelength light needs to be filtered off, this material can fully meet the color requirement for pure blue CIE (0.14, 0.08) in display devices.

Based on the present description, those skilled in the art can understand that various modifications and substitutions of specific embodiments are possible. Therefore, the present description is merely illustrative. It should be understood that the specific examples and embodiments shown and described herein are illustrative. The elements and materials explained and described in the present disclosure can be replaced, the components and procedures may be reversed, and the specific features may be applied independently. For all of those, those skilled in the art will understand from this description. Modifications to the elements described herein can be made without departing from the spirit and scope defined by the claims.

What is claimed is:

1. A platinum complex of Formula I:

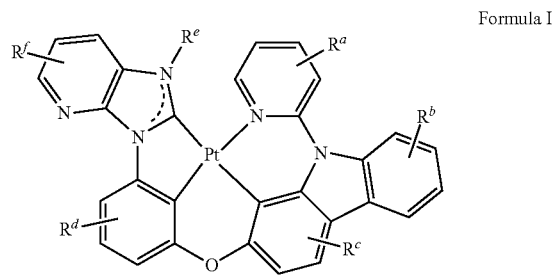

Formula I wherein each of $R^a$, $R^b$, $R^c$, $R^d$ and $R^f$ independently is a 1, 2, 3 or 4 substituents, and each of $R^a$, $R^b$, $R^c$, $R^d$ and $R^f$ is independently selected from: (1) hydrogen atom and its isotopes, and any other monoatomic substituents; or (2) alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, hydroxyl, hydrosulfuryl, nitro, cyano, isocyano, sulphinyl, sulphonyl, carboxyl, hydrazino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, polymeric groups, or substituents containing isotopes;

$R^e$ is selected from alkyl, aryl-substituted alkyl, fluorine-substituted alkyl, aryl, alkyl-substituted aryl, aryl-substituted aryl, or cycloalkyl.

2. The platinum complex according to claim 1, wherein each of $R^a$, $R^b$, $R^c$, $R^d$ and $R^f$ is independently selected from deuterium, tritium, fluorine, chlorine, bromine, or iodine.

3. The platinum complex according to claim 1, wherein each of $R^a$, $R^b$, $R^c$, $R^d$, $R^e$ and $R^f$ is independently selected from methyl, benzyl, diphenylmethyl, triphenylmethyl; ethyl, 2-phenylethyl, 2,2-diphenylethyl, 2,2,2-trifluoroethyl; propyl, isopropyl, 3,3,3-trifluoropropyl, 1,1,1,3,3,3-hexafluoro-2-propyl; butyl, isobutyl, hexafluoroisobutyl, tert-butyl; cyclopropyl, cyclobutyl, cyclopentyl, cyclohexyl, cycloheptyl; phenyl, 2-methylphenyl, 2-isopropylphenyl, 2-ethylphenyl, 4-methylphenyl, 4-isopropylphenyl, 4-ethylphenyl, 4-tert-butylphenyl, 2,4-dimethylphenyl, 2,4-diethylphenyl, 2,4-diisopropylphenyl, 2,6-dimethylphenyl, 3,5-dimethylphenyl, 2,3,5,6-tetramethylphenyl, or 2,4,6-trimethylphenyl.

4. The platinum complex according to claim 1, wherein $R^d$ is selected from hydrogen atom, methyl, isopropyl, or tert-butyl, $R^e$ is selected from methyl, isopropyl, cyclohexyl, cyclopentyl, 2,6-dimethylphenyl, or 2,4,6-trimethylphenyl, and $R^f$ is selected from hydrogen or methyl.

5. The platinum complex according to claim 1, wherein $R^a$ is selected from deuterium, —CDH$_2$, —CD$_2$H, —CD$_3$, —CDR$^1$R$^2$, —CD$_2$R$^1$, wherein each of $R^1$ and $R^2$ is independently selected from alkyl, aryl-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, or polymeric groups.

6. The platinum complex according to claim 1, wherein the platinum complex is selected from:

Complex 1

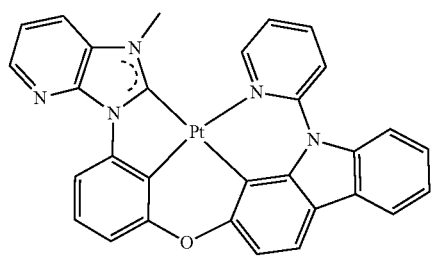

Complex 2

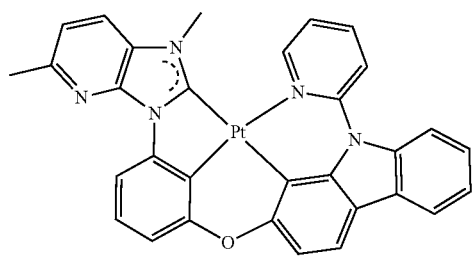

Complex 3

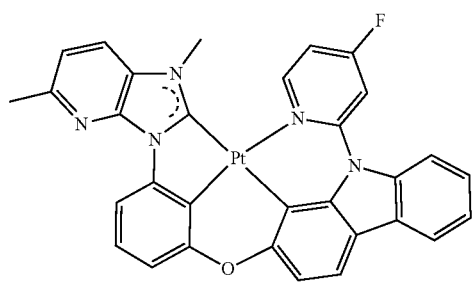

Complex 4

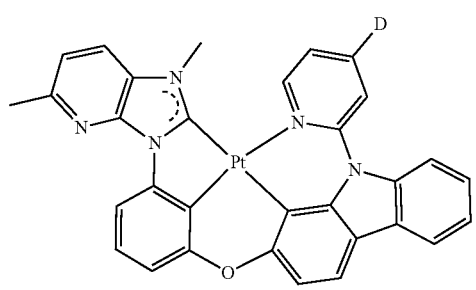

-continued

Complex 5

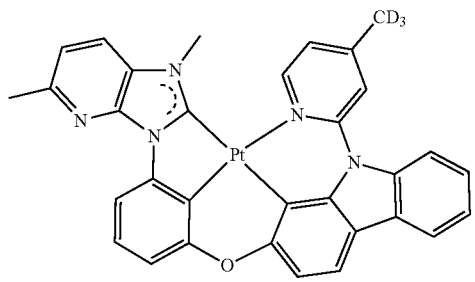

Complex 6

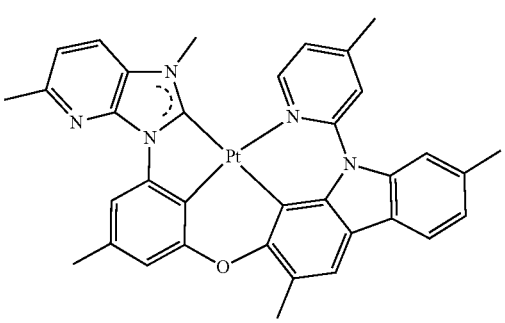

Complex 7

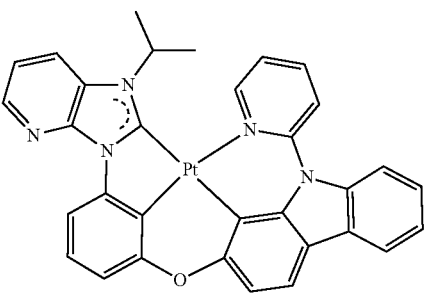

Complex 8

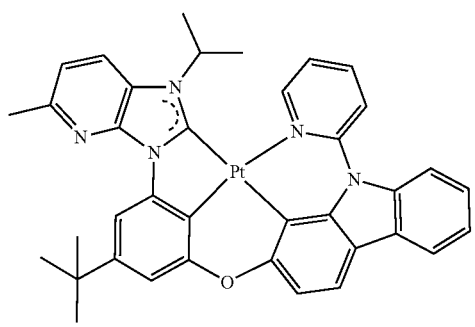

Complex 9

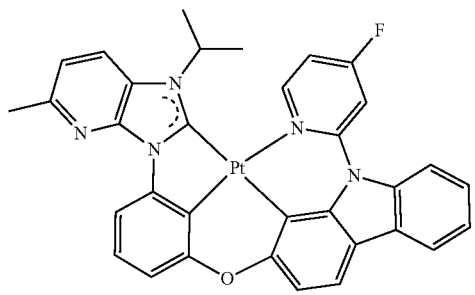

Complex 10
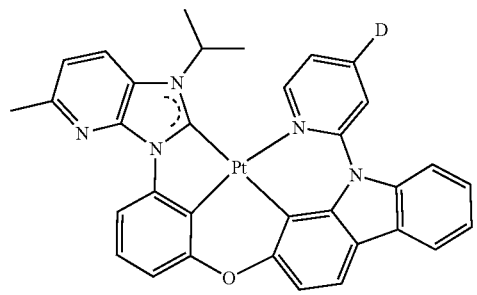
Complex 11
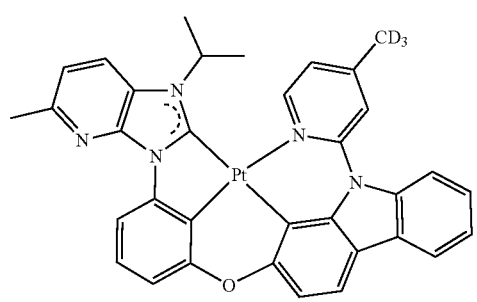
Complex 12
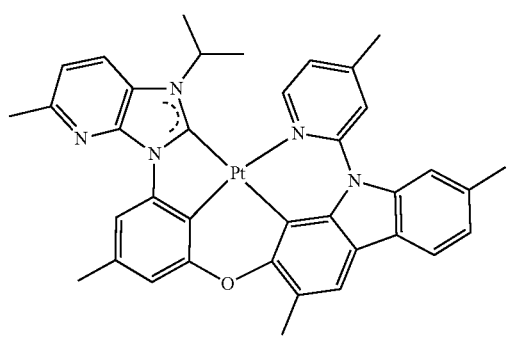
Complex 13
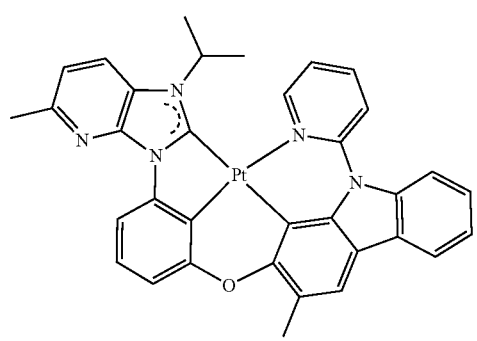
Complex 14
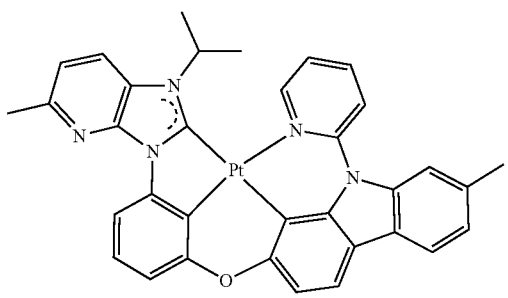
Complex 15
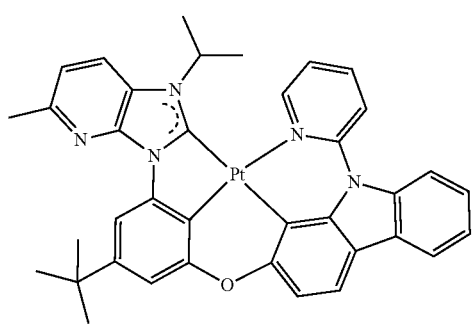
Complex 16
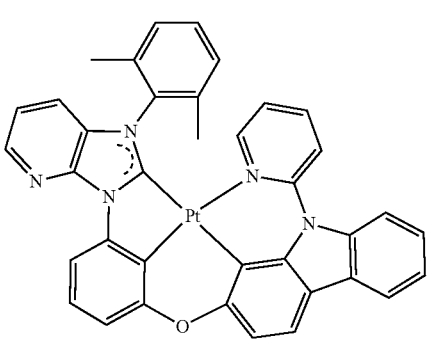
Complex 17
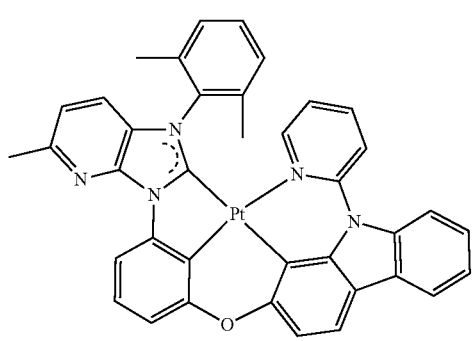

Complex 18
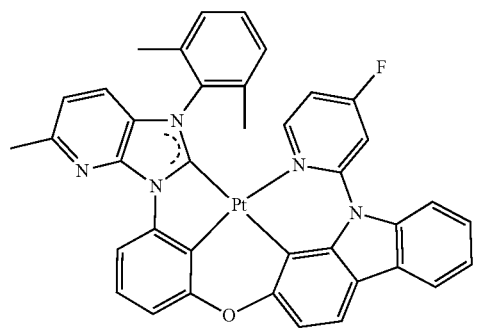
Complex 19
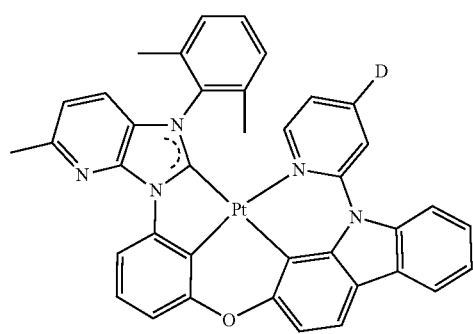
Complex 20
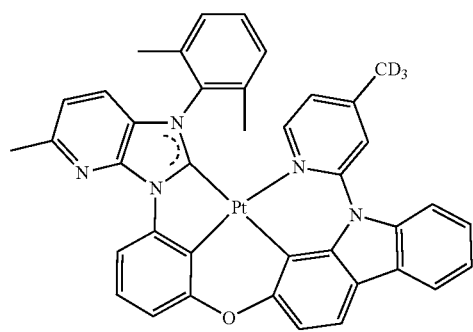
Complex 21
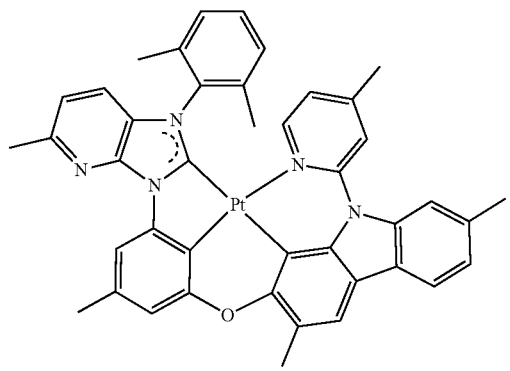
Complex 22
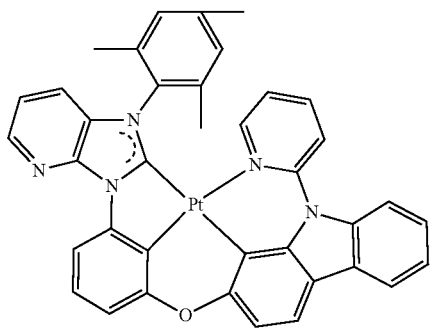
Complex 23
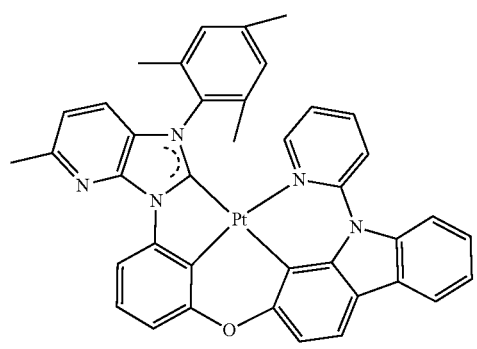
Complex 24
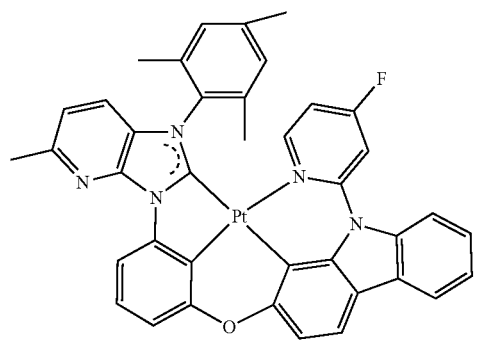
Complex 25
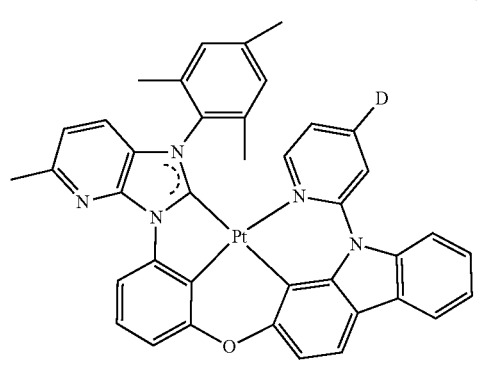

Complex 26
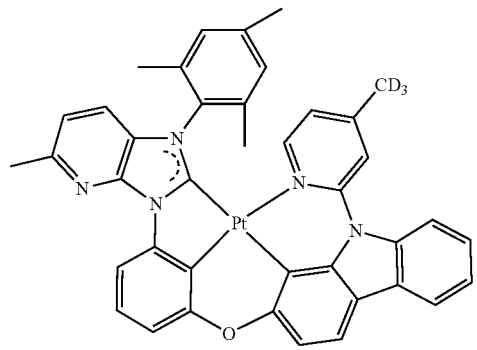

Complex 27
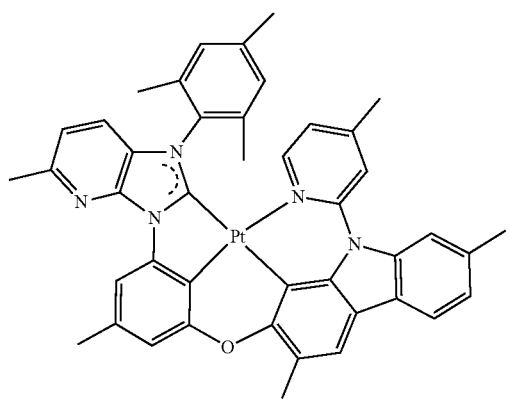

Complex 28
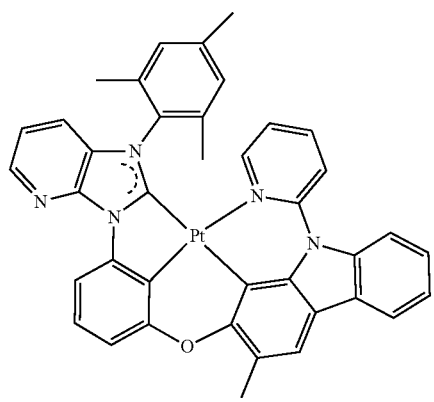

Complex 29
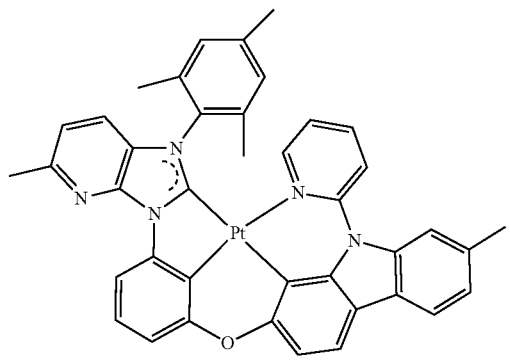

Complex 30
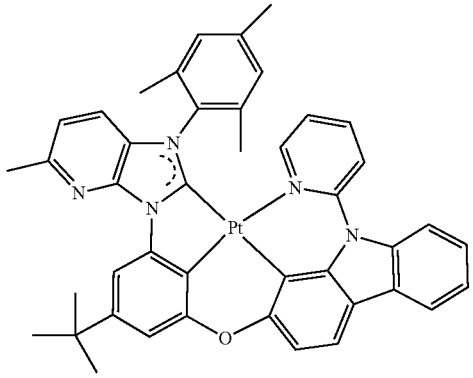

Complex 101
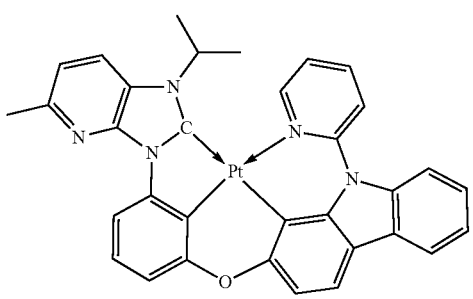

Complex 102
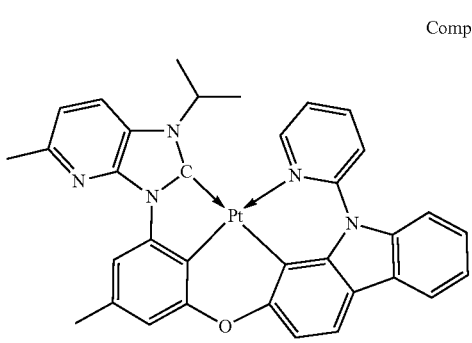

Complex 103
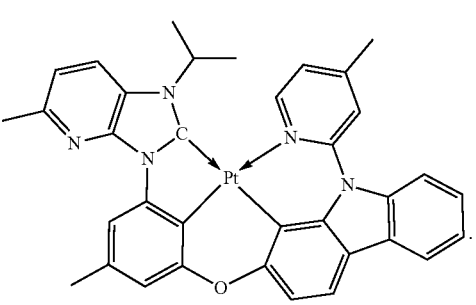

7. The platinum complex according to claim 1, wherein the platinum complex further comprises a bridge structure formed between aromatic rings to which $R^a$ and $R^b$ are bonded respectively, and the bridge structure is selected from —C($R^h$)$_2$—, —Si($R^h$)$_2$—, —O—, or —N$R^h$—, and the platinum complex has a structure of Formula II, Formula III, Formula IV, or Formula V:

Formula II

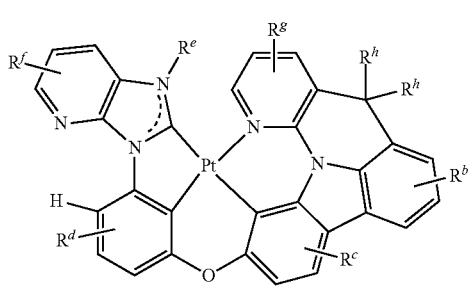

Formula III

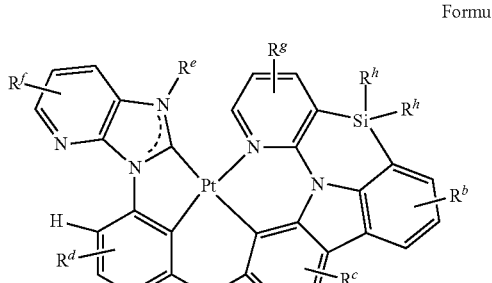

Formula IV

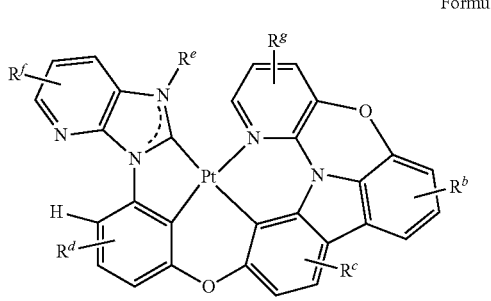

Formula V

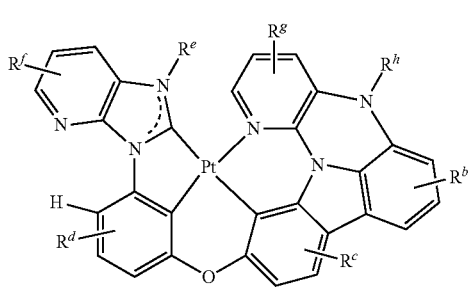

Wherein each of $R^g$ is independently selected from: (1) hydrogen atom, its isotopes, and any other monoatomic substituents; or (2) alkyl, aryl-substituted alkyl, fluorine-substituted alkyl, aryl, alkyl-substituted aryl, aryl-substituted aryl, cycloalkyl, cycloalkenyl, heteroaryl, alkenyl, alkynyl, amino, monohydrocarbylamino, dihydrocarbylamino, diarylamino, monoarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, polymeric groups, or these substituents containing isotopes, such as deuterated methyl;

$R^h$ is selected from alkyl, aryl-substituted alkyl, aryl, alkyl-substituted aryl, aryl-substituted aryl, fluorine-substituted alkyl, fluorine-substituted aryl, cycloalkyl, cycloalkenyl, heteroaryl, alkenyl, alkynyl, amino, monohydrocarbylamino, dihydrocarbylamino, monoarylamino, diarylamino, alkoxy, aryloxy, haloalkyl, ester group, alkoxycarbonyl, acylamino, alkoxycarbonylamino, aryloxycarbonylamino, sulfamoyl, carbamoyl, alkylthio, ureido, phosphoramide group, silyl, polymeric groups, or these substituents containing isotopes.

8. The platinum complex according to claim 7, wherein the platinum complex has a structure 104:

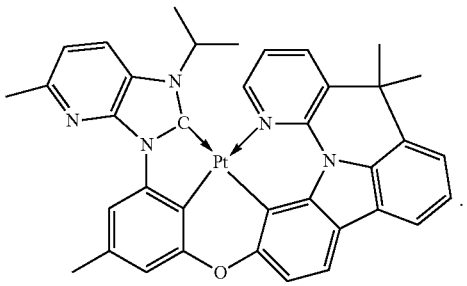

9. The platinum complex according to claim 1 as an electroluminescent material.

10. The platinum complex according to claim 1 as a blue light-emitting material.

11. The platinum complex according to claim 10, wherein the blue light has a wavelength of 450-490 nm.

12. The platinum complex according to claim 1 as a photoluminescent material.

13. The platinum complex according to claim 1 as a phosphorescent material.

14. The platinum complex according to claim 1 as a luminescent material, a host material of the luminescent layer, or a guest material of a luminescent layer in an organic photoelectric device.

15. An organic photoelectric device, comprising a luminescent layer, which comprises the platinum complex according to claim 1.

\* \* \* \* \*